US007566723B2

(12) United States Patent
Gielen-Haertwig et al.

(10) Patent No.: US 7,566,723 B2
(45) **Date of Patent: *Jul. 28, 2009**

(54) 1-PHENYL1-3,4-DIHYDROPYRIMIDIN-2(1H)-ONE DERIVATIVES AND THEIR USE

(75) Inventors: Heike Gielen-Haertwig, Monheim (DE); Volkhart Min-Jian Li, Velbert (DE); Ulrich Rosentreter, Wuppertal (DE); Karl-Heinz Schlemmer, Wuppertal (DE); Swen Allerheiligen, Essen (DE); Leila Telan, Wuppertal (DE); Lars Bärfacker, Oberhausen (DE); Jörg Keldenich, Wuppertal (DE); Mary F. Fitzgerald, Yarnton (GB); Kevin Nash, Herts (GB); Barbara Albrecht, Wülfrath (DE); Dirk Meurer, Pulheim (DE)

(73) Assignee: Bayer Healthcare AG, Leverkusen (DE)

( * ) Notice: Subject to any disclaimer, the term of this patent is extended or adjusted under 35 U.S.C. 154(b) by 197 days.

This patent is subject to a terminal disclaimer.

(21) Appl. No.: 10/527,386

(22) PCT Filed: Aug. 28, 2003

(86) PCT No.: PCT/EP03/09527

§ 371 (c)(1), (2), (4) Date: Nov. 17, 2005

(87) PCT Pub. No.: WO2004/024701

PCT Pub. Date: Mar. 25, 2004

(65) Prior Publication Data

US 2006/0111377 A1 May 25, 2006

(30) Foreign Application Priority Data

Sep. 10, 2002 (GB) ................................ 0220961.7
May 23, 2003 (GB) ................................ 0311957.5

(51) Int. Cl.
*A61K 31/505* (2006.01)
*C07D 239/02* (2006.01)

(52) U.S. Cl. ...................................... 514/269; 544/316

(58) Field of Classification Search ....................... None
See application file for complete search history.

(56) References Cited

U.S. PATENT DOCUMENTS 7,074,993 B1 * 7/2006 Hsieh .......................... 84/327
2008/0021053 A1 * 1/2008 Gielen-Haertwig et al. . 514/274

OTHER PUBLICATIONS

Dandia et. al., Journal of Flourine Chemistry, (1998), 90(1), 17-21.*

Dorwald F. A. Side Reactions in Organic Synthesis, 2005, Wiley: VCH, Weinheim p. IX of Preface.*

Dandia, et al., "Synthesis of Fluorinated Ethyl 4-Aryl-6-Methyl-1,2,3,4-Tetrahydropyrimidin-2-One/Thione-5-Carboxylates Under Microwave Irradiation," *J. Fluorine Chemistry*, 90(1): 17-21 (1998).

Kappe, et al., "Automated Library Generation Using Sequential Microwave-Assisted Chemistry. Application Toward the Biginelli Multicomponent Condensation," *J. Comb. Chem.*, 3 (6): 624-630 (2001).

Barluenga, et al. "A Simple Approach to Pyrimidine and Quinazoline Derivatives By [4+2] Cycloaddition of 1,3-Diazadienes and Enamines," *Heterocycles*, 37 (2): 1109-1120 (1994).

Barluenga, et al., "A Simple Approach to Pyrimidine and Quinazoline Derivatives By [4+2] Cycloaddition of 1,3-Diazadienes and Enamines", Heterocycles 37(2), 1109-1120 (1994).

Khanina, E., "Khimiya Geterotsiklicheskikh Soedinenii", Synthesis and Properties, 90, 1223-1227 (1986).

* cited by examiner

*Primary Examiner*—James O Wilson
*Assistant Examiner*—Jeffrey H Murray
(74) *Attorney, Agent, or Firm*—Edwards Angell Palmer & Dodge LLP; Barry Kramer; Ralph A. Loren

(57) ABSTRACT

The invention relates to novel 1-Phenyl-3,4-dihydropyrimidin-2(1H)-one derivatives having the formula (I-A)

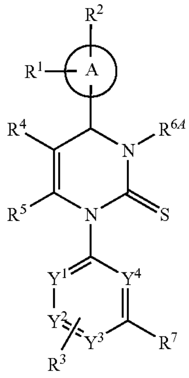

processes for their preparation, and their use in medicaments, especially for the treatment of chronic obstructive pulmonary diseases, acute coronary syndrome, acute myocardial infarction and heart failure development.

11 Claims, No Drawings

1-PHENYL1-3,4-DIHYDROPYRIMIDIN-2(1H)-ONE DERIVATIVES AND THEIR USE

The present invention relates to novel heterocyclic derivatives, processes for their preparation, and their use in medicaments, especially for the treatment of chronic obstructive pulmonary diseases, acute coronary syndrome, acute myocardial infarction and heart failure development.

The fibrous protein elastin, which comprises an appreciable percentage of all protein content in some tissues, such as the arteries, some ligaments, the lungs and the heart, can be hydrolysed or otherwise destroyed by a select group of enzymes classified as elastases. Human leukocyte elastase (HLE, EC 3.4.21.37), also known as human neutrophil elastase (HNE), is a glycosylated, strongly basic serine protease and is found in the azurophilic granules of human polymorphonuclear leukocytes (PMN). HNE is released from activated PMN and has been implicated causally in the pathogenesis of acute and chronic inflammatory diseases. HNE is capable of degrading a wide range of matrix proteins including elastin and collagen, and in addition to these actions on connective tissue HNE has a broad range of inflammatory actions including upregulation of IL-8 gene expression, oedema formation, mucus gland hyperplasia and mucus hypersecretion. It also acts as a mediator of tissue injury by hydrolysing collagen structures, e.g. in the heart after acute myocardial infarction or during the development of heart failure, thus damaging endothelial cells, promoting extravasation of neutrophils adhering to the endothelium and influencing the adhesion process itself.

Pulmonary diseases where HNE is believed to play a role include lung fibrosis, pneumonia, acute respiratory distress syndrome (ARDS), pulmonary emphysema, including smoking-induced emphysema, chronic obstructive pulmonary diseases (COPD) and cystic fibrosis. In cardiovascular diseases, HNE is involved in the enhanced generation of ischaemic tissue injury followed by myocardial dysfunction after acute myocardial infarction and in the remodelling processes occurring during the development of heart failure. HNE has also been causally implicated in rheumatoid arthritis, atherosclerosis, brain trauma, cancer and related conditions in which neutrophil participation is involved.

Thus, inhibitors of HLE activity can be potentially useful in the treatment of a number of inflammatory diseases, especially of chronic obstructive pulmonary diseases [R. A. Stockley, *Neutrophils and protease/antiprotease imbalance*, Am. J. Respir. Crit. Care 160, S49-S52 (1999)]. Inhibitors of HLE activity can also be potentially useful in the treatment of acute myocardial syndrome, unstable angina pectoris, acute myocardial infarction and coronary artery bypass grafts (CABG) [C. P. Tiefenbacher et al., *Inhibition of elastase improves myocardial function after repetitive ischaemia and myocardial infarction in the rat heart*, Eur. J. Physiol. 433, S563-S570 (1997); Dinerman et al., *Increased neutrophil elastase release in unstable angina pectoris and acute myocardial infarction*, J. Am. Coll. Cardiol. 15, 1559-1563 (1990)], of the development of heart failure [S. J. Gilbert et al., *Increased expression of promatrix metalloproteinase-9 and neutrophil elastase in canine dilated cardiomyopathy*, Cardiov. Res. 34, S377-S383 (1997)] and of atherosclerosis [Dollery et al., *Neutrophil elastase in human atherosclerotic plaque*, Circulation 107, 2829-2836 (2003)].

The synthesis of certain 6-methyl-1,4-diphenyl-3,4-dihydro-2(1H)-pyrimidinethione derivatives is described in *J. Comb. Chem.* 3, 624-630 (2001), *J. Fluorine Chem.* 90, 17-21 (1998) and *Khim. Geterotsikd. Soedin.* 9, 1223-1227 (1986) [*Chem. Abstr.* 107, 39737 (1987)]. A specific pharmacological activity of these compounds is not mentioned.

The present invention relates to compounds of the general formulas (I-A) and (I-B)

(I-A)

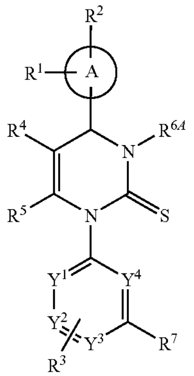

(I-B)

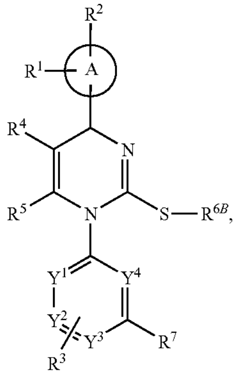

wherein

A represents an aryl or heteroaryl ring, $R^1$, $R^2$ and $R^3$ independently from each other represent hydrogen, halogen, nitro, cyano, $C_1$-$C_6$-alkyl, hydroxy or $C_1$-$C_6$-alkoxy, wherein $C_1$-$C_6$-alkyl and $C_1$-$C_6$-alkoxy can be further substituted with one to three identical or different radicals selected from the group consisting of halogen, hydroxy and $C_1$-$C_4$-alkoxy, $R^4$ represents $C_1$-$C_6$-alkyl, $C_1$-$C_6$-alkylcarbonyl, $C_1$-$C_6$-alkoxycarbonyl, hydroxy-carbonyl, aminocarbonyl, mono- or di-$C_1$-$C_4$-alkylaminocarbonyl, $C_6$-$C_{10}$-arylaminocarbonyl, heteroarylcarbonyl, heterocyclylcarbonyl, heteroaryl, heterocyclyl or cyano, wherein $C_1$-$C_6$-alkyl, $C_1$-$C_6$-alkylcarbonyl, $C_1$-$C_6$-alkoxycarbonyl, mono- and di-$C_1$-$C_4$-alkylaminocarbonyl can be further sub-stituted with one to three identical or different radicals selected from the group consisting of $C_3$-$C_8$-cycloalkyl, hydroxy, $C_1$-$C_4$-alkoxy, $C_1$-$C_4$-alkoxy-carbonyl, hydroxycarbonyl, aminocarbonyl, mono- and di-$C_1$-$C_4$-alkylamino-carbonyl, $C_1$-$C_4$-alkylcarbonylamino, amino, mono- and di-$C_1$-$C_4$-alkylamino, heteroaryl, heterocyclyl, tri-($C_1$-$C_6$-alkyl)-silyl and cyano, $R^5$ represents $C_1$-$C_4$-alkyl, which can be substituted with one to three identical or different radicals selected from the group consisting of halogen, hydroxy, $C_1$-$C_6$-alkoxy, $C_2$-$C_6$-alkenoxy, $C_1$-$C_6$-alkylthio, amino, mono- and di-$C_1$-$C_6$-alkylamino, arylamino, hydroxycarbonyl, $C_1$-$C_6$-alkoxycarbonyl and the radical —O—$C_1$-$C_4$-alkyl-O—$C_1$-$C_4$-alkyl, $R^{6A}$ represents hydrogen, $C_1$-$C_6$-alkylcarbonyl, $C_3$-$C_8$-cycloalkylcarbonyl, $C_1$-$C_6$-alkoxycarbon mono- or di-$C_1$-$C_4$-alkylaminocarbonyl, wherein $C_1$-$C_6$-alkylcarbonyl, $C_1$-$C_6$-alkoxycarbonyl, mono- and di-$C_1$-$C_4$-alkylaminocarbonyl can be substituted with one to three identical or different radicals selected from the group consisting of $C_3$-$C_8$-cycloalkyl, hydroxy, $C_1$-$C_4$-alkoxy, amino, mono- and di-$C_1$-$C_4$-alkylamino, $R^{6B}$ represents $C_1$-$C_6$-alkyl, which can be substituted with one to three identical or different radicals selected from the group consisting of hydroxy, $C_1$-$C_4$-alkoxy, amino, mono- and di-$C_1$-$C_4$-alkylamino, $C_1$-$C_4$-alkoxycarbonyl, hydroxycarbonyl, aminocarbonyl, mono- and di-$C_1$-$C_4$-alkylaminocarbonyl, $C_1$-$C_4$-alkylcarbonyloxy, aminocarbonyloxy, cyano, aryl, heteroaryl and heterocyclyl, wherein heteroaryl and heterocyclyl can be further substituted with one to two identical or different radicals selected from the group consisting of $C_1$-$C_4$-alkyl, hydroxy and oxo, $R^7$ represents halogen, nitro, cyano, $C_1$-$C_6$-alkyl, hydroxy or $C_1$-$C_6$-alkoxy, wherein $C_1$-$C_6$-alkyl and $C_1$-$C_6$-alkoxy can be further substituted with one to three identical or different radicals selected from the group consisting of halogen, hydroxy and $C_1$-$C_4$-alkoxy, and $Y^1$, $Y^2$, $Y^3$ and $Y^4$ independently from each other represent CH or N, wherein the ring contains either 0, 1 or 2 nitrogen atoms.

The compounds according to this invention can also be present in the form of their salts, hydrates and/or solvates.

Physiologically acceptable salts are preferred in the context of the present invention.

Physiologically acceptable salts according to the invention are non-toxic salts which in general are accessible by reaction of the compounds (I) with an inorganic or organic base or acid conventionally used for this purpose. Non-limiting examples of pharmaceutically acceptable salts of compounds (1) include the alkali metal salts, e.g. lithium, potassium and sodium salts, the alkaline earth metal salts such as magnesium and calcium salts, the quaternary ammonium salts such as, for example, triethyl ammonium salts, acetates, benzene sulphonates, benzoates, dicarbonates, disulphates, ditartrates, borates, bromides, carbonates, chlorides, citrates, dihydrochlorides, fumarates, gluconates, glutamates, hexyl resorcinates, hydrobromides, hydro-chlorides, hydroxynaphthoates, iodides, isothionates, lactates, laurates, malates, maleates, mandelates, mesylates, methylbromides, methylnitrates, methylsulphates, nitrates, oleates, oxalates, palmitates, pantothenates, phosphates, diphosphates, polygalacturonates, salicylates, stearates, sulphates, succinates, tartrates, tosylates, valerates, and other salts used for medicinal purposes.

Hydrates of the compounds of the invention or their salts are stoichiometric compositions of the compounds with water, such as for example hemi-, mono-, or dihydrates.

Solvates of the compounds of the invention or their salts are stoichiometric compositions of the compounds with solvents.

The present invention includes both the individual enantiomers or diastereomers and the corresponding racemates or diastereomeric mixtures of the compounds according to the invention and their respective salts. In addition, all possible tautomeric forms of the compounds described above are included according to the present invention. The diastereomeric mixtures can be separated into the individual isomers by chromatographic processes. The racemates can be resolved into the respective enantiomers either by chromatographic processes on chiral phases or by resolution.

In the context of the present invention, the substituents, if not stated otherwise, in general have the following meaning:

Alkyl in general represents a straight-chain or branched hydrocarbon radical having 1 to 6, preferably 1 to 4 carbon atoms. Non-limiting examples include methyl, ethyl, n-propyl, isopropyl, n-butyl, isobutyl, sec.-butyl, tert.-butyl, pentyl, isopentyl, hexyl, isohexyl. The same applies to radicals such as alkoxy, alkylthio, alkylamino, alkyl-carbonyl, alkoxycarbonyl and alkoxycarbonylamino.

Alkoxy illustratively and preferably represents methoxy, ethoxy, n-propoxy, iso-propoxy, tert.-butoxy, n-pentoxy and n-hexoxy.

Alkenoxy illustratively and preferably represents allyloxy, but-2-en-1-oxy, pent-3-en-1-oxy und hex-2-en-1-oxy.

Alkylthio illustratively and preferably represents methylthio, ethylthio, n-propylthio, isopropylthio, tert.-butylthio, n-pentylthio and n-hexylthio.

Alkylcarbonyl in general represents a straight-chain or branched hydrocarbon radical having 1 to 6, preferably 1 to 4 carbon atoms which is bonded via a carbonyl group. Non-limiting examples include acetyl, n-propionyl, n-butyryl, isobutyryl, pivaloyl, n-hexanoyl.

Alkylcarbonylamino in general represents a straight-chain or branched hydrocarbon lodical having 1 to 6, preferably 1 to 4 carbon atoms which has a carbonylamino (—CO—NH—) function at the position of attachment and which is bonded to the carbonyl group. Non-limiting examples include acetylamino, n-propionylamino, n-butyryl-amino, isobutyrylamino, pivaloylamino, n-hexanoylamino.

Alkylcarbonyloxy in general represents a straight-chain or branched hydrocarbon radical having 1 to 6, preferably 1 to 4 carbon atoms which has a carbonyloxy (—CO—O—) function at the position of attachment and which is bonded to the carbonyl group. Non-limiting examples include acetyloxy, n-propionyloxy, n-butyryloxy, iso-butyryloxy, pivaloyloxy, n-hexanoyloxy.

Cycloalkyl in general represents a cyclic saturated hydrocarbon radical having 3 to 8, preferably 3 to 6 carbon atoms. Non-limiting examples include cyclopropyl, cyclobutyl, cyclopentyl, cyclohexyl and cycloheptyl.

Cycloalkylcarbonyl represents a cycloalkyl radical having 3 to 8, preferably 3 to 6 ring carbon atoms which is bonded via a carbonyl group, illustratively and preferably representing cyclopropylcarbonyl, cyclobutylcarbonyl, cyclopentylcarbonyl, cyclohexyl-carbonyl and cycloheptylcarbonyl.

Alkoxycarbonyl illustratively and preferably represents methoxycarbonyl, ethoxy-carbonyl, n-propoxycarbonyl, isopropoxycarbonyl, tert.-butoxycarbonyl, n-pentoxy-carbonyl and n-hexoxycarbonyl.

Alkylamino represents an alkylamino radical having one or two (independently selected) alkyl substituents, illustratively and preferably representing methylamino, ethylamino, n-propylamino, isopropylamino, tert.-butylamino, n-pentylamino, n-hexyl-amino, N,N-dimethylamino, N,N-diethylamino, N-ethyl-N-methylamino, N-methyl-N-n-propylamino, N-isopropyl-N-n-propylamino, N-tert.-butyl-N-methylamino, N-ethyl-N-n-pentylamino and N-n-hexyl-N-methylamino.

Alkylaminocarbonyl represents an alkylaminocarbonyl radical having one or two (independently selected) alkyl substituents, illustratively and preferably representing methylaminocarbonyl, ethylaminocarbonyl, n-propylaminocarbonyl, isopropylamino-carbonyl tert.-butylaminocarbonyl, n-pentylaminocarbonyl, n-hexylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl, N-tert.-butyl-N-methylaminocarbonyl, N-ethyl-N-n-pentylaminocarbonyl and N-n-hexyl-N-methylaminocarbonyl.

Aryl represents a mono- to tricyclic aromatic carbocyclic radical having generally 6 to 14 carbon atoms, illustratively and preferably representing phenyl, naphthyl and phenanthrenyl. The same applies to radicals such as arylamino.

Heteroaryl per se and in heteroarylcarbonyl represents an aromatic mono- or bicyclic radical having generally 5 to 10 and preferably 5 or 6 ring atoms and up to 5 and preferably up to 4 heteroatoms selected from the group consisting of S, O and N, illustratively and preferably representing thienyl, furyl, pyrrolyl, thiazolyl, oxazolyl, isothiazolyl, isoxazolyl, imidazolyl, pyridyl, pyrimidyl, pyridazinyl, indolyl, indazolyl, benzofuranyl, benzothiophenyl, quinolinyl, isoquinolinyl.

Heteroarylcarbonyl illustratively and preferably represents thienylcarbonyl, furyl-carbonyl, pyrrolylcarbonyl, thiazolylcarbonyl, oxazolylcarbonyl, isoxazolylcarbonyl, imidazolylcarbonyl, pyridylcarbonyl, pyrimidylcarbonyl, pyridazinylcarbonyl, indolyl-carbonyl, indazolylcarbonyl, benzofuranylcarbonyl, benzothiophenylcarbonyl, quino-linylcarbonyl, isoquinolinylcarbonyl.

Heterocyclyl per se and in heterocyclylcarbonyl represents a mono- or polycyclic, preferably mono- or bicyclic, nonaromatic heterocyclic radical having generally 4 to 10 and preferably 5 to 8 ring atoms and up to 3 and preferably up to 2 heteroatoms and/or hetero groups selected from the group consisting of N, O, S, SO and $SO_2$. The heterocyclyl radicals can be saturated or partially unsaturated. Preference is given to 5- to 8-membered monocyclic saturated heterocyclyl radicals having up to two heteroatoms selected from the group consisting of O, N and S, such as illustratively and preferably tetrahydrofuranyl, pyrrolidinyl, piperidinyl, morpholinyl, thio-morpholinyl, piperazinyl, perhydroazepinyl.

Heterocyclylcarbonyl illustratively and preferably represents tetrahydrofiran-carbonyl, pyrrolidinecarbonyl, piperidinecarbonyl, morpholinecarbonyl, thiomorpho-linecarbonyl, piperazinecarbonyl, perhydroazepinecarbonyl.

Halogen represents fluorine, chlorine, bromine and iodine.

When stated, that $Y^1$, $Y^2$, $Y^3$ and $Y^4$ represent CH or N, CH shall also stand for a ring carbon atom, which is substituted with a substituent $R^3$.

In another embodiment, the present invention relates to compounds of general formulas (I-A) and (I-B), wherein A represents an aryl or heteroaryl ring, $R^1$, $R^2$ and $R^3$ independently from each other represent hydrogen, halogen, nitro, cyano, $C_1$-$C_6$-alkyl, hydroxy or $C_1$-$C_6$-alkoxy, wherein $C_1$-$C_6$-alkyl and $C_1$-$C_6$-alkoxy can be further substituted with one to three identical or different radicals selected from the group consisting of halogen, hydroxy and $C_1$-$C_4$-alkoxy, $R^4$ represents $C_1$-$C_6$-alkylcarbonyl, $C_1$-$C_6$-alkoxycarbonyl, hydroxycarbonyl, aminocarbonyl, mono- or di-$C_1$-$C_4$-alkylaminocarbonyl, $C_6$-$C_{10}$-arylamino-carbonyl, heteroarylcarbonyl, heterocyclylcarbonyl, heteroaryl, heterocyclyl or cyano, wherein $C_1$-$C_6$-alkylcarbonyl, $C_1$-$C_6$-alkoxycarbonyl, mono- and di-$C_1$-$C_4$-alkylaminocarbonyl can be further substituted with one to three identical or different radicals selected from the group consisting of $C_3$-$C_8$-cycloalkyl, hydroxy, $C_1$-$C_4$-alkoxy, $C_1$-$C_4$-alkoxycarbonyl, hydroxycarbonyl, aminocarbonyl, mono- and di-$C_1$-$C_4$-alkylaminocarbonyl, $C_1$-$C_4$-alkyl-carbonylamino, amino, mono- and di-$C_1$-$C_4$-alkylamino, heteroaryl, heterocyclyl and tri-($C_1$-$C_6$-alkyl)-silyl, $R^5$ represents $C_1$-$C_4$-alkyl, which can be substituted with one to three identical or different radicals selected from the group consisting of halogen, hydroxy, $C_1$-$C_6$-alkoxy, $C_2$-$C_6$-alkenoxy, $C_1$-$C_6$-alkylthio, amino, mono- and di-$C_1$-$C_6$-alkylamino, arylamino, hydroxycarbonyl, $C_1$-$C_6$-alkoxycarbonyl and the radical —O—$C_1$-$C_4$-alkyl-O—$C_1$-$C_4$-alkyl, $R^{6A}$ represents hydrogen, $C_1$-$C_6$-alkylcarbonyl, $C_3$-$C_8$-cycloalkylcarbonyl, $C_i$-$C_6$-alkoxycarbonyl, mono- or di-$C_1$-$C_4$-alkylaminocarbonyl, wherein $C_1$-$C_6$-alkylcarbonyl, $C_1$-$C_6$-alkoxycarbonyl, mono- and di-$C_1$-$C_4$-alkylaminocarbonyl can be substituted with one to three identical or different radicals selected from the group consisting of $C_3$-$C_8$-cycloalkyl, hydroxy, $C_1$-$C_4$-alkoxy, amino, mono- and di-$C_1$-$C_4$-alkylamino, $R^{6B}$ represents $C_1$-$C_6$-aklyl, which can be substituted with one to three identical or different radicals selected from the group consisting of hydroxy, $C_1$-$C_4$-alkoxy, amino, mono- and di-$C_1$-$C_4$-alkylamino, aryl, heteroaryl and hetero-cyclyl, $R^7$ represents halogen, nitro, cyano, $C_1$-$C_6$-alkyl, hydroxy or $C_1$-$C_6$-alkoxy, wherein $C_1$-$C_6$-alkyl and $C_1$-$C_6$-alkoxy can be further substituted with one to three identical or different radicals selected from the group consisting of halogen, hydroxy and $C_1$-$C_4$-alkoxy, and $Y^1$, $Y^2$, $Y^3$ and $Y^4$ independently from each other represent CH or N, wherein the ring contains either 0, 1 or 2 nitrogen atoms.

In another embodiment, the present invention relates to compounds of general formulas (I-A) and (I-B), wherein A represents a phenyl or pyridyl ring, $R^1$, $R^2$ and $R^3$ independently from each other represent hydrogen, fluoro, chloro, bromo, nitro, cyano, methyl, ethyl, trifluoromethyl or trifluoromethoxy, $R^4$ represents $C_1$-$C_6$-alkylcarbonyl, $C_1$-$C_6$-alkoxycarbonyl, hydroxycarbonyl, aminocarbonyl, mono- or di-$C_1$-$C_4$-alkylaminocarbonyl or cyano, wherein $C_1$-$C_6$-alkylcarbonyl, $C_1$-$C_6$-aloxycarbonyl and mono-$C_1$-$C_4$-alkylaminocarbonyl can be substituted with one to three identical or different radicals selected from the group consisting of $C_3$-$C_6$-cycloalkyl, hydroxy, $C_1$-$C_4$-alkoxy, $C_1$-$C_4$-alkoxycarbonyl, amino, mono- or di-$C_1$-$C_4$-alylamino, heteroaryl and heterocyclyl, $R^5$ represents methyl or ethyl, $R^{6A}$ represents hydrogen, $C_1$-$C_6$-alkylcarbonyl or $C_3$-$C_6$-cycloalkylcarbonyl, wherein $C_1$-$C_6$-alkylcarbonyl can be substituted with a radical selected from the group consisting of $C_3$-$C_6$-cycloalkyl, hydroxy, $C_1$-$C_4$-alkoxy, amino, mono- and di-$C_1$-$C_4$-alkylamino, $R^{6B}$ represents $C_1$-$C_6$-alkyl, which can be substituted with a radical selected from the group consisting of hydroxy, $C_1$-$C_4$-alkoxy, amino, mono- and di-$C_1$-$C_4$-alkylamino, phenyl, heteroaryl and heterocyclyl, $R^7$ represents halogen, nitro, cyano, trifluoromethyl, trifluoromethoxy, methyl or ethyl, and $Y^1$, $Y^2$, $Y^3$ and $Y^4$ each represent CH.

In another embodiment, the present invention relates to compounds of general formulas (I-A) and (I-B), wherein A represents a phenyl or a pyridyl ring, $R^1$ and $R^3$ each represent hydrogen, $R^2$ represents fluoro, chloro, bromo, nitro or cyano, $R^4$ represents $C_1$-$C_4$-alkylcarbonyl or $C_1$-$C_4$-alkoxycarbonyl, wherein $C_1$-$C_4$-alk-oxycarbonyl can be substituted with a radical selected from the group consisting of hydroxy, $C_1$-$C_4$-alkoxy, $C_1$-$C_4$-alkoxycarbonyl, mono- and di-$C_1$-$C_4$-alkylamino, heteroaryl and heterocyclyl, $R^5$ represents methyl, $R^{6A}$ represents hydrogen, $C_1$-$C_6$-alkylcarbonyl or $C_3$-$C_6$-cycloalkylcarbonyl, $R^{6b}$ represents $C_1$-$C_4$-alkyl, which can be substituted with a radical selected from the group consisting of hydroxy, $C_1$-$C_4$-alkoxy, amino, di-$C_1$-$C_4$-alkylamino, phenyl, pyridyl, imidazolyl, pyrrolidino and morpholino, $R^7$ represents trifluoromethyl or nitro, and $Y^1$, $Y^2$, $Y^3$ and $Y^4$ each represent CH.

In another embodiment, the present invention relates to compounds according to general formulas (I-A) and (I-B), wherein A is phenyl or pyridyl.

In another embodiment, the present invention relates to compounds according to general formulas (I-A) and (I-B), wherein $R^1$ is hydrogen.

In another embodiment, the present invention relates to compounds according to general formulas (I-A) and (I-B), wherein $R^2$ is cyano, especially wherein A is phenyl or pyridyl and $R^2$ is cyano located in para-position relative to the central di-hydropyrimidinthione ring.

In another embodiment, the present invention relates to compounds according to general formulas (I-A) and (I-B), wherein $R^3$ is hydrogen.

In another embodiment, the present invention relates to compounds according to general formulas (I-A) and (I-B), wherein $R^4$ is $C_1$-$C_4$-alkoxycarbonyl, which can be substituted with dimethylamino, diethylamino, N-ethylmethylamino, pyrrolidino or piperidino, or wherein $R^4$ is $C_1$-$C_4$-alkylcarbonyl, especially methylcarbonyl. In another embodiment, the present invention relates to compounds according to general formulas (I-A) and (I-B), wherein $R^5$ is methyl.

In another embodiment, the present invention relates to compounds according to general formula (I-A), wherein $R^{6A}$ is hydrogen.

In another embodiment, the present invention relates to compounds according to general formula (I-B), wherein $R^{6B}$ is methyl, (1H-imidazol-2-yl)methyl, 2-(diethyl-amino)ethyl, 2-hydroxyethyl, 3-hydroxypropyl and 2-(1-pyrrolidinyl)ethyl.

In another embodiment, the present invention relates to compounds according to general formulas (I-A) and (I-B), wherein $R^7$ is trifluoromethyl or nitro.

In another embodiment, the present invention relates to compounds of general formula (I-C)

(I-C)

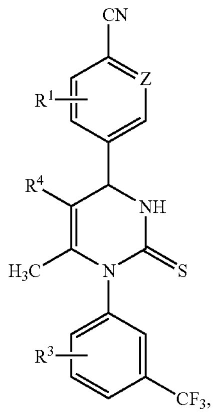

wherein

Z represents CH or N, and $R^1$, $R^3$ and $R^4$ have the meaning indicated above.

In another embodiment, the present invention relates to compounds of general formula (I-E)

(I-E)

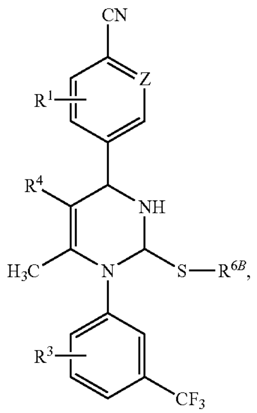

wherein

Z represents CH or N, $R^1$, $R^3$ and $R^4$ have the meaning indicated above, and $R^{6B}$ represents $C_1$-$C_4$-alkyl, which can be substituted with a radical selected from the group consisting of hydroxy, di-$C_1$-$C_4$-alkylamino, phenyl, pyridyl, imidazolyl, pyrrolidino and morpholino.

The compounds of the present invention, wherein $R^{6A}$ in general formula (I-A) is hydrogen, can enolize into the corresponding mercaptoamidines:

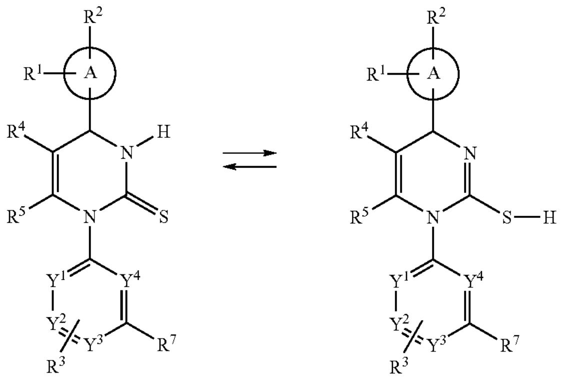

The compounds of general formulas (I-A), (I-B), (I-C) and (I-E), respectively, can be synthesized by condensing compounds of general formula (II)

(II)

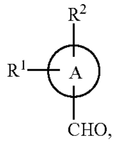

wherein A, $R^1$ and $R^2$ have the meaning indicated above, with compounds of general formula (III)

(III)

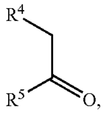

wherein $R^4$ and $R^5$ have the meaning indicated above, and compounds of general formula (IV)

(IV)

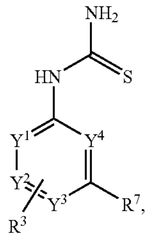

wherein $R^3$, $R^7$, and $Y^1$ to $Y^4$ have the meaning indicated above, in the presence of an acid either in a three-component/one-step reaction or sequentially to give compounds of the general formula (I-D)

(I-D)

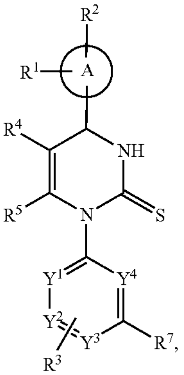

wherein

A, $R^1$to $R^5$, $R^7$, and $Y^1$ to $Y^4$ have the meaning indicated above, optionally followed by reaction of the compounds of general formula (I-D) in the presence of a base either

[A] with compounds of the general formula (V)

$$R^{6A*}—X^{A} \quad (V),$$

wherein $R^6$* has the meaning of $R^{6A}$ as indicated above, but does not represent hydrogen, and $X^A$ represents a leaving group, such as halogen, to give compounds of the general formula (I-A) or (I-C), respectively, or

[B] with compounds of the general formula (VI)

$$R^{6B}—X^{B} \quad (VI),$$

wherein $R^{6B}$ has the meaning indicated above and $X^B$ represents a leaving group, such as halogen, tosylate, mesylate or sulfate, to give compounds of the general formula (I-B) or (I-E), respectively.

Suitable solvents for the process (II)+(III)+(IV)→(I-D) are generally customary organic solvents which do not change under the reaction conditions. These include ethers such as diethyl ether, diisopropyl ether, 1,2-dimethoxyethane, dioxan or tetrahydroflran, ethyl acetate, acetone, acetonitrile, dimethylsulfoxide, dimethyl-formamide, or alcohols such as methanol, ethanol, n-propanol, isopropanol, n-butanol or t-butanol, or hydrocarbons such as pentane, hexane, cyclohexane, benzene, toluene or xylene, or halogeno-hydrocarbons such as dichloromethane, dichloroethane, trichloromethane or chlorobenzene. It is also possible to use mixtures of the above-mentioned solvents. Preferred for the process is tetrahydrofuran.

Suitable acids for the process (II)+(III)+(IV)→(I-D) are generally inorganic or organic acids. These preferably include carboxylic acids, such as, for example, acetic acid or trifluoroacetic acid, sulfonic acids, such as, for example, methanesulfonic acid or p-toluenesulfonic acid, hydrochloric acid or phosphoric acids such as poly-phosphoric acids. Preference is given to polyphosphoric acid ethyl ester or polyphosphoric acid trimethylsilyl ester. The acid is employed in an amount from 0.25 mol to 100 mol, relative to 1 mol of the compound of the general formula (III).

The process is in general carried out in a temperature range from +20° C. to +150° C., preferably from +60° C. to +100° C.

The process is generally carried out at normal pressure. However, it is also possible to carry it out at elevated pressure or at reduced pressure (for example in a range from 0.5 to 5 bar).

Suitable solvents for the process (I-D)+(V)→(I-A)/(I-C) are generally customary organic solvents which do not change under the reaction conditions. These include ethers such as diethyl ether, diisopropyl ether, 1,2-dimethoxyethane, dioxan or tetra-hydrofuran, ethyl acetate, acetone, acetonitrile, dimethylsulfoxide, dimethylform-amide, or halogeno-hydrocarbons such as dichloromethane, dichloroethane, tri-chloromethane or chlorobenzene. It is also possible to use mixtures of the above-mentioned solvents. Preferred for the process is tetrahydrofuran.

Suitable bases for the process (I-D)+(V)→(I-A)/(I-C) are generally inorganic or organic bases. These preferably include cyclic amines, such as, for example, piperidine, pyridine or 4N,N-dimethylaminopyridine, or ($C_1$-$C_4$)-trialkylamines, such as, for example, triethylamine or diisopropylethylamine. Preference is given to pyridine. The base is employed in an amount from 0.1 mol to 10 mol, preferably from 1 mol to 3 mol, relative to 1 mol of the compound of general formula (I-D).

The process is in general carried out in a temperature range from −20° C. to +120° C., preferably from +0° C. to +80° C., especially at room temperature.

The process is generally carried out at normal pressure. However, it is also possible to carry it out at elevated pressure or at reduced pressure (for example in a range from 0.5 to 5 bar).

Suitable solvents for the process (I-D)+(VI)→(I-B)/(I-E) are generally customary organic solvents which do not change under the reaction conditions. These include ethers such as diethyl ether, diisopropyl ether, 1,2-dimethoxyethane, dioxan or tetra-hydrofuran, ethyl acetate, acetone, acetonitrile, dimethylsulfoxide, dimethylform-amide, or halogeno-hydrocarbons such as dichloromethane, dichloroethane, tri-chloromethane or chlorobenzene. It is also possible to use mixtures of the above-mentioned solvents. Preferred for the process is acetone.

Suitable bases for the process (I-D)+(VI)→(I-B)/(I-E) are generally inorganic or organic bases. These preferably include alkali hydroxides, such as lithium, sodium or potassium hydroxide, alkali or alkaline-earth carbonates, such as sodium, potassium, calcium or caesium carbonate, alkali alkoxides, such as sodium or potassium methoxide, sodium or potassium ethoxide, or sodium or potassium tert.-butoxide, or cyclic amines, such as piperidine, pyridine or 4-N,N-dimethylaminopyridine, or $(C_1-C_4)$-trialkylamines, such as triethylamine or diisopropylethylamine, or hydrides such as sodium hydride. Preference is given to potassium carbonate. The base is employed in an amount from 0.1 mol to 10 mol, preferably from 1 mol to 3 mol, relative to 1 mol of the compound of general formula (I-D).

To enhance the reactivity of the compounds of general formula (VI) in cases where $X^B$ is chloride or bromide, the process (I-D)+(VI)→(I-B)/(I-E) is preferably carried out in the presence of catalytic amounts of iodide sources, such as potassium iodide or tetralutylammonium iodide.

The process is in general carried out in a temperature range from 0° C. to +150° C., preferably from +0° C. to +80° C., especially at room temperature.

The process is generally carried out at normal pressure. However, it is also possible to carry it out at elevated pressure or at reduced pressure (for example in a range from 0.5 to 5 bar).

The compounds of the general formulas (II), (III), (I), (V) and (VI) are known per se, or they can be prepared by customary methods.

The above-mentioned method can be illustrated by the following scheme:

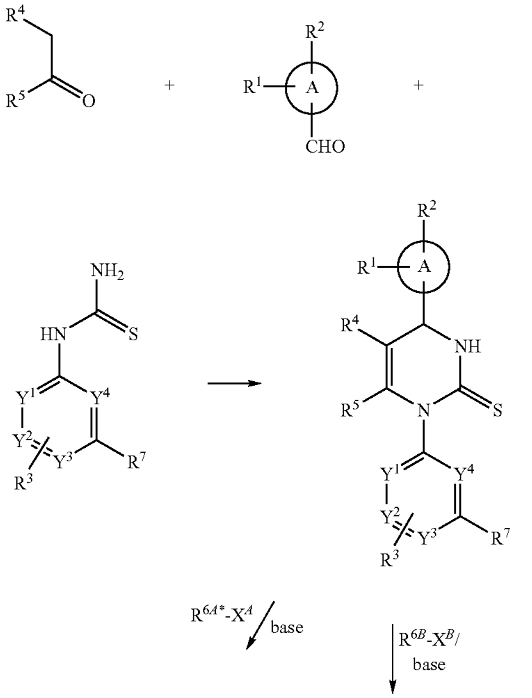

-continued

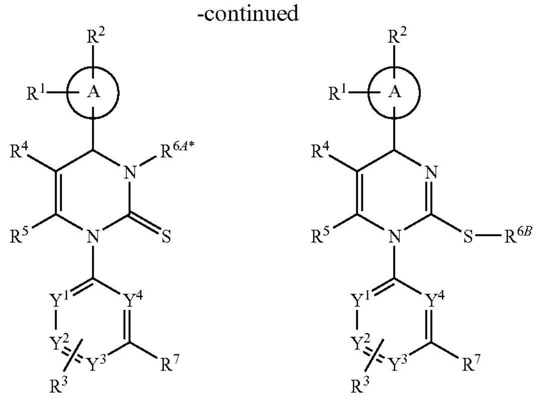

The compounds according to the invention exhibit an unforeseeable, useful pharmacological and pharmacokinetic activity spectrum. They are therefore suitable for use as medicaments for the treatment and/or prophylaxis of disorders in humans and animals.

Surprisingly, the compounds of the present invention show human neutrophil elastase (HNE) inhibitory activity and are therefore suitable for the preparation of medicaments for the treatment of diseases associated with HNE activity. They may thus provide an effective treatment of acute and chronic inflammatory processes, such as rheumatoid arthritis, atherosclerosis, and especially of acute and chronic pulmonary diseases, such as lung fibrosis, cystic fibrosis, pneumonia, acute respiratory distress syndrome (ARDS), in particular pulmonary emphysema, including smoking-induced emphysema, and chronic obstructive pulmonary diseases (COPD), chronic bronchitis and bronchiectasis. The compounds of the present invention may further provide an effective treatment for cardiovascular ischaemic diseases such as acute coronary syndrome, acute myocardial infarction, unstable and stable angina pectoris, coronary artery bypass grafts (CABG) and heart failure development, for atherosclerosis, mitral valvular disease, atrial septal defects, percutaneous transluminal coronary angioplasty O?TCA), inflammation after open heart surgery and for pulmonary hypertension. They may also prove useful for an effective treatment of rheumatoid arthritis, acute inflammatory arthritis, cancer, acute pancreatitis, ulcerative colitis, periodontal disease, Chury-Strauss syndrome, acute and chronic atopic dermatitis, psoriasis, systemic lupus erythematosus, bullous pemphigus, sepsis, alcoholic hepatitis, liver fibrosis, Behcet's disease, allergic fungal sinusitis, allergic sinusitis, Crohn's disease, Kawasaki disease, glomerulonephritis, acute pyelonephritis, colorectal diseases, chronic suppurative otitis media, chronic venous leg ulcers, inflammatory bowel disease, bacterial and viral infections, brain trauma, stroke and other conditions in which neutrophil participation is involved.

The present invention further provides medicaments containing at least one compound according to the invention, preferably together with one or more pharma-cologically safe excipient or carrier substances, and also their use for the above-mentioned purposes.

The active component can act systemically and/or locally. For this purpose, it can be applied in a suitable manner, for example orally, parenterally, pulmonally, nasally, sublingually, lingually, buccally, rectally, transdermally, conjunctivally, otically or as an implant.

For these application routes, the active component can be administered in suitable application forms.

Useful oral application forms include application forms which release the active component rapidly and/or in modified form, such as for example tablets (non-coated and coated tablets, for example with an enteric coating), capsules, sugar-coated tablets, granules, pellets, powders, emulsions, suspensions, solutions and aerosols. Parenteral application can be carried out with avoidance of an absorption step (intravenously, intraarterially, intracardially, intraspinally or intralumbarly) or with inclusion of an absorption (intramuscularly, subcutaneously, intracutaneously, percutaneously or intraperitoneally). Useful parenteral application forms include injection and infusion preparations in the form of solutions, suspensions, emulsions, lyophilisates and sterile powders.

Forms suitable for other application routes include for example inhalatory pharmaceutical forms (including powder inhalers, nebulizers), nasal drops/solutions, sprays; tablets or capsules to be administered lingually, sublingually or buccally, suppositories, ear and eye preparations, vaginal capsules, aqueous suspensions (lotions, shake mixtures), lipophilic suspensions, ointments, creams, rnilk, pastes, dusting powders or implants.

The active components can be converted into the recited application forms in a manner known per se. This is carried out using inert non-toxic, pharmaceutically suitable excipients. These include inter alia carriers (for example microcrystalline cellulose), solvents (for example liquid polyethylene glycols), emulsifiers (for example sodium dodecyl sulphate), dispersing agents (for example polyvinyl-pyrrolidone), synthetic and natural biopolymers (for example albumin), stabilizers (for example antioxidants such as ascorbic acid), colorants (for example inorganic pigments such as iron oxides) or taste and/or odor corrigents.

For human use, in the case of oral administration, it is recommendable to administer doses of from 0.001 to 50 mg/kg, preferably of 0.01 mg/kg to 20 mg/kg. In the case of parenteral administration, such as, for example, intravenously or via mucous membranes nasally, buccally or inhalationally, it is recommendable to use doses of 5 0.001 mg/kg to 0.5 mg/kg.

In spite of this, it can be necessary in certain circumstances to depart from the amounts mentioned, namely as a function of body weight, application route, individual behaviour towards the active component, manner of preparation and time or interval at which application takes place. It can for instance be sufficient in some cases to use less than the aforementioned minimum amount, while in other cases the upper limit mentioned will have to be exceeded. In the case of the application of larger amounts, it can be advisable to divide them into a plurality of individual doses spread through the day.

The percentages in the tests and examples which follows are, unless otherwise stated, by weight; parts are by weight. Solvent ratios, dilution ratios and concentrations reported for liquid/liquid solutions are each based on the volume.

A. Evaluation of Physiological Activity

The potential of the compounds of the invention to inhibit neutrophil elastase activity may be demonstrated, for example, using the following assays:

I. In vitro Enzyme Assays of Human Neutrophil Elastase (HNE)

Assay Contents assay buffer: 0.1 M HEPES-NaOH buffer pH 7.4, 0.5 M NaCl, 0.1% (w/v) bovine serum albumin;

suitable concentration (see below) of HNE (18 U/mg lyophil., #20927.01, SERVA Electrophoresis GmbH, Heidelberg, Germany) in assay buffer;

suitable concentration (see below) of substrate in assay buffer;

suitable concentration of test compounds diluted with assay buffer from a 10 mM stock solution in DMSO.

EXAMPLE A

In vitro Inhibition of HNE Using a Fluorogenic Peptide Substrate (Continuous Read-out Signal, 384 MTP Assay Format):

In this protocol, the elastase substrate MeOSuc-Ala-Ala-Pro-Val-AMC (#324740, Calbiochem-Novabiochem Corporation, Merck KGaA, Darmstadt, Germany) is used. The test solution is prepared by mixing 10 μl of test compound dilution, 20 μl of HNE enzyme dilution (final concentration 8-0.4 μU/ml, routinely 2.1 μU/ml) and 20 μl of substrate dilution (final concentration 1 mM-1 μM, routinely 20 μM), respectively. The solution is incubated for 0-2 hrs at 37° C. (routinely one hour). The fluorescence of the liberated AMC due to the enzymatic reaction is measured at 37° C. (TECAN spectra fluor plus plate reader). The rate of increase of the fluorescence (ex. 395 mm. 460 nm) is proportional to elastase activity. $IC_{50}$ values are determined by RFU-versus-[I] plots. $K_m$ and $K_{m(app.)}$ values are determined by Lineweaver-Burk plots and converted to $K_i$ values by Dixon plots.

The preparation examples had $IC_{50}$ values within the range of 5 nM-5 μM in this assay. Representative data are given in Table 1:

TABLE 1

| Example No. | $IC_{50}$ [nM] |
|---|---|
| 1 | 13 |
| 3 | 9 |
| 4 | 23 |
| 6 | 70 |
| 7 | 10 |
| 9 | 40 |
| 12 | 100 |
| 14 | 10 |
| 15 | 5 |
| 19 | 30 |
| 29 | 10 |
| 31 | 80 |
| 33 | 20 |
| 58 | 12 |

EXAMPLE B

In vitro Inhibition of HNE Using a Fluorogenic, Unsoluble Elastin Substrate (Discontinuous Read-out Signal, 96 MTP Assay Format):

In this protocol the elastase substrate elastin-fluorescein (#100620, ICN Biomedicals GmbH, Eschwege, Germany) is used. The test solution is prepared by mixing 3 μl of test compound dilution, 77 μl of HNE enzyme dilution (final concentration 0.22 U/ml-2.2 mU/ml, routinely 21.7 μU/ml) and 80 μl substrate suspension (final concentration 2 mg/mi). The suspension is incubated for 0-16 hrs at 37° C. (routinely four hours) under slightly shaking conditions. To stop the enzymatic reaction, 160 μl of 0.1 M acetic acid are added to the test solution (final concentration 50 mM). The polymeric elastin-fluorescein is pulled down by centrifugation (Eppendorf 5804 centrifuge, 3.000 rpm, 10 nm). The supernatant is transferred into a new MIP and the fluorescence of the liberated peptide fluorescein due to the enzymatic reaction is measured (BMG Fluostar plate reader). The rate of fluorescence (ex. 490 nm, em. 520 nm) is proportional to elastase activity. $IC_{50}$ values are determined by RFU-versus-[I] plots.

II. In vitro Human Neutrophil Assays

EXAMPLE A

In vitro PMN Elastolysis Assay:

This assay is used to determine the elastolytic potential of human polymorphonuclear cells (PMNs) and assess the proportion of degradation due to neutrophil elastase [cf. Z. W. She et al., Am. J. Respir. Cell. Mol. Biol. 9, 386-392 (1993)].

Tritiated elastin, in suspension, is coated on to a 96 well plate at 10 μg per well. Test and reference [ZD-0892 (J. Med. Chem. 40, 1876-1885, 3173-3181 (1997), WO 95/21855) and α1 protease inhibitor (α1PI)] compounds are added to the wells at the appropriate concentrations. Human PMNs are separated from peripheral venous blood of healthy donors and resuspended in culture media The neutrophils are added to the coated wells at concentrations ranging between $1\times10^6$ to $1\times10^5$ cells per well. Porcine pancreatic elastase (1.3 μM) is used as a positive control for the assay, and α1PI (1.2 μM) is used as the positive inhibitor of neutrophil elastase. The cellular control is PMNs without compound at each appropriate cell density. The cells plus compounds are incubated in a humidified incubator at 37° C. for 4 hours. The plates are centrifuged to allow the harvest of cell supematant only. The supernatant is transferred in 75 μl volumes to corresponding wells of a 96 well Lumaplate™ (solid scintillant containing plates). The plates are dried until no liquid is visible in the wells and read in a beta counter for 3 minutes per well.

Elastolysis of the $^3$H-elastin results in an increase in counts in the supernatant. An inhibition of this elastolysis shows a decrease, from the cellular control, of tritium in the supernatant. α1PI gave 83.46±3.97% (mean±s.e.m.) inhibition at 1.2 μM (n=3 different donors at $3.6\times10^5$ cells per well). $IC_{50}$ values were obtained for the reference compound ZD-0892 of 45.50±7.75 nM (mean±s.e.m.) (n=2 different donors at $3.6\times10^5$ cells per well).

Given that ZD-0892 is a selective inhibitor of PMN elastase along with the data from α1PI inhibition, these results indicate that the majority of elastin degradation by PMNs is due to the release of neutrophil elastase, and not to another elastolytic enzyme such as matrix metalloproteases (MMPs). The compounds of this invention are evaluated for their inhibitory activity in this HNE-dependent model of neutrophil elastolysis.

EXAMPLE B

In vitro Inhibition of Membrane Bound Elastase:

Measurement of the inhibition of elastase bound to neutrophil membranes is performed using a human neutrophil assay. Neutrophils are stimulated with LPS at 37° C. for 35 min and then spun at 1600 rpm. Subsequently, the membrane bound elastase is fixed to the neutrophils with 3% paraformaldehyde and 0.25% glutaraldehyde for 3 min at 4° C. The neutrophils are then spun, and vehicle and the compound under evaluation are added, followed by addition of the substrate MeO-Suc-Ala-Ala-Pro-Val-AMC (#324740, Calbiochem-Novabiochem Corporation, Merck KGaA, Darmstadt, Germany) at 200 μM. Following a 25 min incubation at 37° C., the reaction is terminated with PMSF (phenyhnethanesulfonyl fluoride), and the fluorescence is read at ex: 400 nm and em: 505 nm. $IC_{50}$ values are determined by interpolation from plots of relative fluorescence vs. inhibitor concentration.

III. In vivo Models

EXAMPLE A

In vivo Model of Acute Lung Injury in the Rat:

Instillation of human neutrophil elastase (HNE) into rat lung causes acute lung damage. The extent of this injury can be assessed by measuring lung haemorrhage.

Rats are anaesthetised with Hypnorm/Hypnovel/water and instilled with HNE or saline delivered by microsprayer into the lungs. Test compounds are administered by intravenous injection, by oral gavage or by inhalation at set times prior to the administration of HNE. Sixty minutes after the administration of elastase animals are killed by an anaesthetic overdose (sodium pentobarbitone) and the lungs lavaged with 2 ml heparinised phosphate buffered saline (PBS). Bronchoalveolar lavage (BAL) volume is recorded and the samples kept on ice. Each BAL sample is centrifuged at 900 r.p.m. for 10 minutes at 4-10° C. The supernatant is discarded and the cell pellet resuspended in PBS and the sample spun down again. The supernatant is again discarded and the cell pellet resuspended in 1 ml 0.1% cetyltrimethyl-ammonium bromide (CTAB)/PBS to lyse the cells. Samples are frozen until blood content is assayed. Prior to the haemorrhage assay the samples are defrosted and mixed. 100 μl of each sample are placed into a separate well of a 96 well flat-bottomed plate. All samples are tested in duplicate. 100 μl 0.1% CTAB/PBS is included as a blank. The absorbance of the well contents is measured at 415 nm using a spectrophotometer. A standard curve is constructed by measuring the OD at 415 nm of different concentrations of blood in 0.1% CTAB/PBS. Blood content values are calculated by comparison to the standard curve (included in each plate) and normalised for the volume of BAL fluid retrieved.

The compounds of this imvention are evaluated intravenously, orally or by inhalation for their inhibitory activity in this model of HNE-induced haemorrhage in the rat.

EXAMPLE B

In vivo Model of Acute Myocardial Infarction in the Rat:

Elastase inhibitors are tested in a rat thread infarct model. Male Wistar rats (weighing >300 g) receive 10 mg/kg aspirin 30 min prior to surgery. They are anaesthetized by isofluran and ventilated (120-130 strokes/min,.200-250 μl stroke volume; MiniVent Type 845, Hugo Sachs Elektronik, Germany) during the whole surgery. Following a left thoracotomy at the fourth intercostal space, the pericardium is opened and the heart briefly exteriorized. A thread is turned around the left coronary artery (LAD) without occluding the artery. The thread is passed under the skin to the neck of the animal. The thorax is closed and the animal is allowed to recover for 4 days. At the fifth day, rats are anaesthetized with ether for 3 min, and the thread is tied and the LAD occluded under ECG control. Test compounds are administered before or after LAD occlusion per os, intraperitoneally or intravenously (bolus or permanent infusion). After 1 hr occlusion, the thread is reopened to allow reperfusion. Hearts are excised, and infarct sizes are determined 48 hours later by staining of the reoccluded hearts with Evans blue, followed by TTC (triphenyltetrazolium chloride) staining of 2 mm heart sections. Normoxic (not occluded tissue) areas stain blue, ischemic (occluded but surviving tissue) areas stain red and necrotic (occluded dead tissue) areas remain white. Each tissue section is scanned and infarct sizes are determined by computer planimetry.

B. EXAMPLES

Abbreviations:

DMU N,N-dimethylfobramide
DMSO dimethylsulfoxide
EI electron-impact ionisation (for MS)
ESI electro-spray ionisation (for MS)
h hour(s)
HPLC high pressure liquid chromatography
LC-MS liquid chromatography coupled with mass spectroscopy
MS mass spectroscopy
NMR nuclear magnetic resonance
of th. of theoretical (yield)
RP reverse phase (for HPLC)
$R_t$ retention time (for HPLC)
THF tetrahydrofuran General Methods:

All reactions were carried out under an argon atmosphere unless otherwise noted. Solvents were used as purchased from commercial sources without further purification. 'Silica gel' or 'Silica' refers to Silica gel 60 (0.040 mm-0.063 mm) from Merck KGaA company, Germany. Compounds purified over preparative HPLC were purified over a RP18-column with acetonitrile and water as the eluent, using a 1:9 to 9:1 gradient.

LC-MS and HPLC Methods:

Method 1:

Instrument: Micromass Platform LCZ, HP1100; Column: Symmetry C18, 50 mm×2.1 mm, 3.5 μm; Eluent A: water+0.05% formic acid, Eluent B: acetonitrile+0.05% formic acid; Gradient: 0.0 min 90% A→4.0 min 10% A→6.0 min 10% A; Oven: 40° C.; Flow: 0.5 ml/min; UV-detection: 208-400 nm.

Method 2:

Instrument MS: Micromass ZQ; Instrument HPLC: Waters Alliance 2790; Column: Uptisphere HDO, 50 mm×2.0 mm, 3.0 μm; Eluent A: water+0.05% formic acid, Eluent B: acetonitrile+0.05% formic acid; Gradient: 0.0 min 5% B→2.0 min 40% B→4.5 min 90% B→5.5 min 90% B; Temperature: 45° C.; Flow: 0.75 ml/min; UV-detection: 210 nm.

Method 3:

Instrument: Micromass Platform LCZ, HP1100; Column: Grom-Sil 120 ODS-4 HE, 50 mm×2.0 mm, 3 μm; Eluent A: water+0.05% formic acid, Eluent B: acetonitrile+0.05% formic acid; Gradient: 0.0 min 100% A→0.2 min 100% A→2.9 min 30% A→3.1 min 10% A→4.5 min 10% A; Temperature: 55° C.; Flow: 0.8 ml/min; UV-detection: 208-400 nm.

Method 4:

Instrument: Micromass Quattro LCZ with HPLC Agilent Series 1100; Column: Uptisphere HDO, 50 mm×2.0 mm, 3 μm; Eluent A: 11 water+1 ml 50% formic acid, Eluent B: 11 acetonitrile+1 ml 50% formic acid; Gradient: 0.0 min 100% A→0.2 min 100% A→2.9 min 30% A→3.1 min 10% A→4.5 min 10% A; Temperature: 55° C.; Flow: 0.8 ml/min; UV-detection: 208-400 nm.

Method 5:

Instrument MS: Micromass ZQ; Instrument HPLC: Waters Alliance 2790; Column: Grom-Sil 120 ODS-4 HE 50 mm×2 mm, 3.0 μm; Eluent B: acetonitrile+0.05% formic acid, Eluent A: water+0.05% formic acid; Gradient: 0.0 min 5% B→2.0 min 40% B→4.5 min 90% B→5.5 min 90% B; Temperature: 45° C.; Flow: 0.0 min 0.75 ml/min→4.5 min 0.75 ml/min→5.5 min 1.25 ml/min; UV-detection: 210 nm.

Method 6:

Instrument MS: Micromass ZQ; Instrument HPLC: HP 1100 Series; UV DAD; Column: Grom-Sil 120 ODS-4 HE, 50 mm×2 mm, 3.0 μm; Eluent A: water+500 μl 50% formic acid/1, Eluent B: acetonitrile+500 μl 50% formic acid/1; Gradient: 0.0 min 0% B→2.9 min 70% B→3.1 min 90% B→4.5 min 90% B; Temperature: 50° C.; Flow: 0.8 ml/min; UV-detection: 210 nm.

Method 7:

Instrument: Micromass Platform LCZ with HPLC Agilent Series 1100; Column: Grom-Sil 120 ODS-4 HE, 50 mm×2.0 mm, 3 μm; Eluent A: 11 water+1 ml formic acid (50%), Eluent B: 11 acetonitrile+1 ml formic acid (50%); Gradient: 0.0 min 100% A→0.2 min 100% A→2.9 min 30% A→3.1 min 10% A→4.5 min 10% A; Temperature: 55° C.; Flow: 0.8 mi/min; UV-detection: 208-400 nm.

Method 8:

Instrument: Micromass TOF-MUX-Interface quadruple parallel injection with HPLC Waters 600; Column: Uptisphere HDO, 50 mm×2.0 mm, 3.0 μm; Eluent A: 11 water+1 ml formic acid (50%), Eluent B: 11 acetonitrile+1 ml formic acid (50%); Gradient: 0.0 min 100% A→0.2 min 100% A→2.9 min 30% A→3.1 min 10% A→4.5 min 10% A→4.6 min 100% A→6.5 min 100% A; Temperature: room temperature; Flow: 0.8 ml/min; UV-detection: 210 nm.

PREPARATION EXAMPLES

Example 1

4-{5-Acetyl-6-methyl-2-thioxo-1-[3-(trifluoromethyl)phenyl]-1,2,3,4-tetrahydro-4-pyrimidinyl}benzonitrile

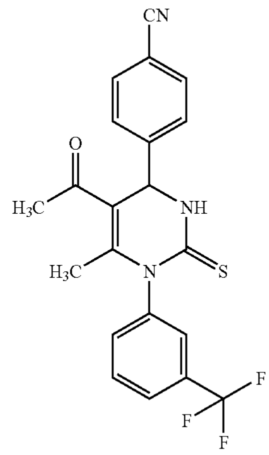

3-Trifluoromethylphenyl thiourea (200 mg, 0.91 mol), 4-cyanobenzaldehyde (238.2 mg, 1.82 mmol) and 2,4-pentanedione (181.9 mg, 1.82 mmol) are dissolved in 5 ml THF. Ethyl polyphosphate (0.30 g) is added and the reaction mixture is stirred at reflux temperature overnight. After cooling to room temperature, the reaction is quenched with 10 ml of water and extracted with 10 ml ethyl acetate (2×). The combined organic layers are dried with sodium sulfate and the solvent is removed in vacuo. The product is purified via preparative HPLC (RP18-column; eluent: acetonitrile-water, gradient 10:90 to 90:10).

Yield: 53 mg (14% of th.) LC-MS (method 1): $R_t$=4.48 min. MS (ESIpos): m/z=416 $(M+H)^+$ $^1$H-NMR (200 MHz, DMSO-$d_6$): δ=10.32 (d, 1H); 7.93 (d, 2H); 7.43-7.84 (m, 6H); 5.48 (d, 1H); 2.26 (s, 3H); 1.99 (s, 3H) ppm.

Example 2

Methyl 4-(4-cyanophenyl)-6-methyl-2-thioxo-1-[3-(trifluoromethyl)phenyl]-1,2,3,4-tetrahydro-5-pyrimidinecarboxylate

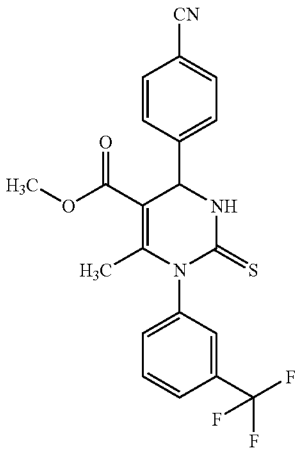

3-Trifluoromethylphenyl thiourea (200 mg, 0.91 mmol), 4-cyanobenzaldehyde (238.2 mg, 1.82 mmol) and methyl acetoacetate (211 mg, 1.82 mmol) are dissolved in 5 ml THF. Ethyl polyphosphate (0.30 g) is added and the reaction mixture is stirred at reflux temperature overnight. After cooling to room temperature, the reaction is quenched with 10 ml of water and extracted with 10 ml ethyl acetate (2×). The combined organic layers are dried with sodium sulfate and the solvent is removed in vacuo. The product is purified via preparative HPLC (RP18-column; eluent: acetonitrile-water, gradient 10:90 to 90:10).

Yield: 315 mg (80% of th.) LC-MS (method 1): $R_t$=4.70 min. MS (ESIpos): m/z=432 $(N+H)^+$ $^1$H-NMR (200 MHz, DMSO-$d_6$): δ=10.24 (d, 1H); 7.92 (d, 2H); 7.54-7.83 (m, 6H); 5.40 (d, 1H); 3.63 (s, 3H); 2.06 (s, 3H) ppm.

Example 3

Ethyl 4-(4-cyanophenyl)-6-methyl-2-thioxo-1-[3-(trifluoromethyl)phenyl]-1,2,3,4-tetrahydro-5-pyrimidinecarboxylate

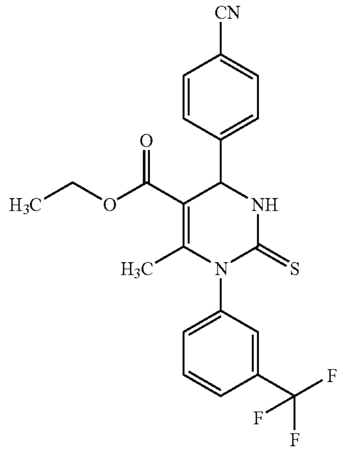

3-Trifluoromethylphenyl thiourea (3.00 g, 13.6 mmol), 4-cyanobenzaldehyde (3.57 g, 27.3 mmol) and ethyl acetoacetate (3.55 g, 27.3 mmol) are dissolved in 50 ml THF. Ethyl polyphosphate (4.50 g) is added and the reaction mixture is stirred at reflux temperature overnight. After cooling to room temperature, it is quenched with 50 ml of water and extracted with 100 ml ethyl acetate (2×). The combined organic layers are dried with sodium sulfate and the solvent is removed in vacua. The product is purified via preparative HPLC (RP18-column; eluent: acetonitrile-water, gradient 10:90 to 90:10).

Yield: 3.15 g (52% of th.) LC-MS (method 2): $R_t$=4.10 min. MS CESIpos): m/z=446 $(M+H)^+$ $^1$H-NMR (200 MHz, DMSO-$d_6$): δ=10.18 (d, 1H); 7.92 (d, 2H); 7.45-7.82 (m, 6H); 5.40 (d, 1H); 4.08 (q, 2H); 2.05 (s, 3H); 1.12 (t, 3H) ppm.

Example 4

4-(4-Cyanophenyl)-6-methyl-2-thioxo-1-[3-(trlfluoromethyl)phenyl]-1,2,3,4-tetra-hydro-5-pyrimidinecarboxamide

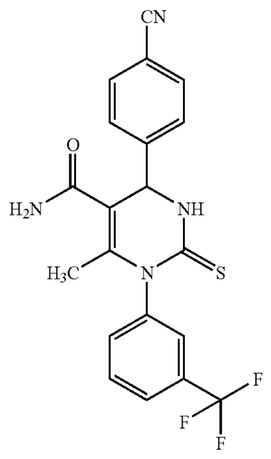

3-Trifluoromethylphenyl thiourea (200 mg, 0.91 mmol), 4-cyanobenzaldehyde (238.2 mg, 1.82 mmol) and 3-oxobutanamide (183 mg, 1.82 mmol) are dissolved in 5 ml THF. Ethyl polyphosphate (0.30 g) is added and the reaction mixture is stirred at reflux temperature overnight. After cooling to room temperature, it is quenched with 10 ml of water and extracted with 10 ml ethyl acetate (2×). The combined organic layers are dried with sodium sulfate and the solvent is removed in vacuo. The product is purified via preparative HPLC (RP18-column; eluent: acetonitrile-water, gradient 10:90 to 90:10).

Yield: 29 mg (8% of th.) LC-MS (method 1): $R_t$=4.35 min. MS (ESIpos): m/z=417 $(M+H)^{+1}$H-NMR (200 MHz, DMSO-$d_6$): δ=9.86 (d, 1H); 7.93 (d, 2H); 7.76 (d, 1H); 7.67 (t, 1H); 7.24-7.62 (m, 4H); 7.59 (d, 2H); 5.40 (d, 1H); 1.74 (s, 3H) ppm.

Example 5

4-(4-Cyanophenyl)-N,6 dimethyl-2-thioxo-1-[3-(trirluoromethyl)phenyl]-1,2,3,4-tetrahydro-5-pyrimidinecarboxamide

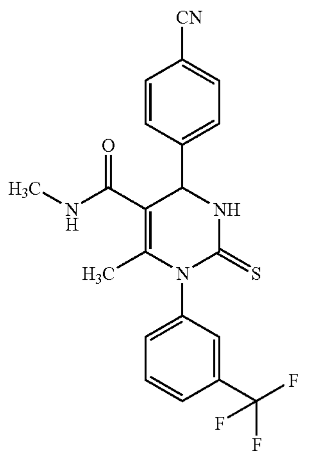

3-Trifluoromethylphenyl thiourea (200 mg, 0.91 mmol), 4-cyanobenzaldehyde (238.2 mg, 1.82 mmol) and N-methyl-3-oxobutanamide (299 mg, 1.82 mmol) are dissolved in 5 ml THF. Ethyl polyphosphate (0.30 g) is added and the reaction mixture is stirred at reflux temperature overnight. After cooling to room temperature, the reaction is quenched with 10 ml of water and extracted with 10 ml ethyl acetate (2×). The combined organic layers are dried with sodium sulfate and the solvent is removed in vacuo. The product is purified via preparative HPLC (RP18-column; eluent: acetonitrile-water, gradient 10:90 to 90:10).

Yield: 104 mg (27% of th.) LC-MS (method 1): $R_t$=4.10 min MS (ESIpos): m/z=431 $(M+H)^{+1}$H-NMR (200 MHz, DMSO-$d_6$): δ=9.89 (d, 1H); 7.93 (d, 2H); 7.54 (d, 2H); 7.38-8.12 (m, 5H); 5.36 (d, 1H); 2.59 (d, 3H); 1.66 (s, 3H) ppm.

Example 6

4-(4-Cyanophenyl)-N,N,6-trimethyl-2-thioxo-1-[3-(trifluoromethyl)phenyl]-1,2,3,4-tetrahydro-5-pyrimidinecarboxamiide

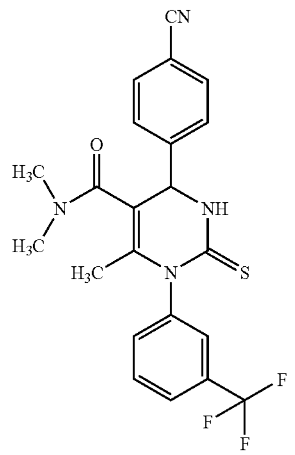

3-Trifluoromethylphenyl thiourea (200 mg, 0.91 mmol), 4-cyanobenzaldehyde (238.2 mg, 1.82 mmol) and N,N-dimethyl-3-oxobutanamide (235 mg, 1.82 mmol) are dissolved in 5 ml THF. Ethyl polyphosphate (0.30 g) is added and the reaction mixture is stirred at reflux temperature overnight. After cooling to room temperature, it is quenched with 10 ml of water and extracted with 10 ml ethyl acetate (2×). The combined organic layers are dried with sodium sulfate and the solvent is removed in vacuo. The product is purified via preparative HPLC (RP18-column; eluent: aceto-nitrile-water, gradient 10:90 to 90:10).

Yield: 270 mg (67% of th.) LC-MS (method 1): $R_t$=4.20 min. MS (ESIpos): m/z=445 $(M+M)^{+1}$H-NMR (200 MHz, DMSO-$d_6$): δ=9.77 (d, 1H); 7.92 (d, 2H); 7.54 (d, 2H); 7.49-7.83 (m, 4H); 5.19 (br. s, 1H); 3.33 (s, 3H); 2.78 (s, 3H); 1.43 (s, 3H) ppm.

Example 7

Ethyl 4-(4-cyanophenyl)-6-methyl-2-(methylsulfanyl)-1-[3-(trifluoromethyl)phenyl]-1,4-dihydro-5-pyrimidinecarboxylate

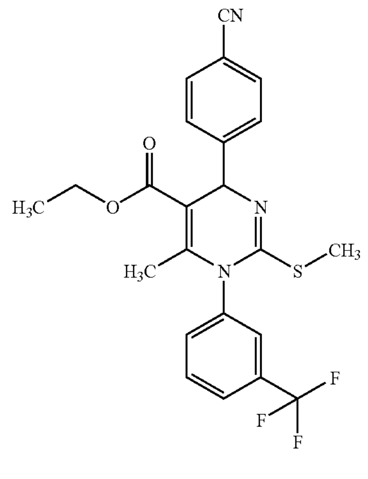

Ethyl 4-(4-cyanophenyl)-6-methyl-2-thioxo-1-[3-(trifluoromethyl)phenyl]-1,2,3,4-tetrahydro-5-pyrimidinecarboxylate (Example 3; 1000 mg, 2.24 mmol), iodomethane (350.5 mg, 2.47 mmol) and potassium carbonate (341 mg, 1.82 mmol) are dissolved in 20 ml acetone. The reaction mixture is stirred at room temperature overnight and the solvent is removed in vacuo. The product is purified by column chromatography (silica gel; eluent: cyclohexane-ethyl acetate, gradient 90:10 to 50:50).

Yield: 998 mg (97% of th.) LC-MS (method 3): $R_t$=4.20 min. MS (ESIpos): m/z=460 $(M+H)^+$ $^1$H-NMR (200 MHz, DMSO-$d_6$): δ=7.85 (d, 2H); 7.69-7.94 (m, 4H); 7.60 (d, 2H); 5.76 (s, 1H); 4.04 (q, 2H); 2.14 (s, 3H); 2.01 (s, 3H); 1.11 (t, 3H) ppm.

Example 8

Methyl 4-(4-cyanophenyl)-6-methyl-2-(methylsulfanyl)1-[3-(truoromethyl)-phenyl]-1,4-dihydro-5-pyrimidinecarboxylate

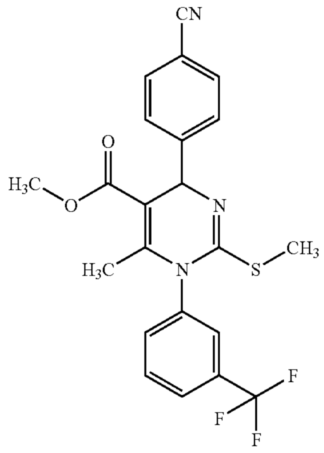

Ethyl 4-(4-cyanophenyl)-6-methyl-2-(methylsulfanyl)-1-[3-(trifluoromethyl)phenyl]-1,4-dihydro-5-pyrimidinecarboxylate (Example 7; 100 mg, 0.22 mmol) and sodium methoxide (117.6 mg, 2.18 mmol) are dissolved in 5 ml methanol and stirred at reflux temperature for 3 h. The reaction is quenched with 10 ml of water and the aqueous phase is extracted with 10 ml methylene chloride (2×). After drying with sodium sulfate, the solvent is removed in vacuo and the product is purified by column chromatography (silica gel; eluent: cyclohexane-ethyl acetate, gradient 90:10 to 50:50).

Yield: 60 mg (62% of th.) LC-MS (method 2): $R_t$=4.27 min. LC-MS (ESIpos): m/z=446 $(M+H)^+$.

Example 9

Ethyl 4-(4-cyanophenyl)-6-methyl-2-(ethylsulfanyl)-1-[3-trifluoromethyl)phenyl]-1,4-dihydro-5-pyrimidinecarboxylate

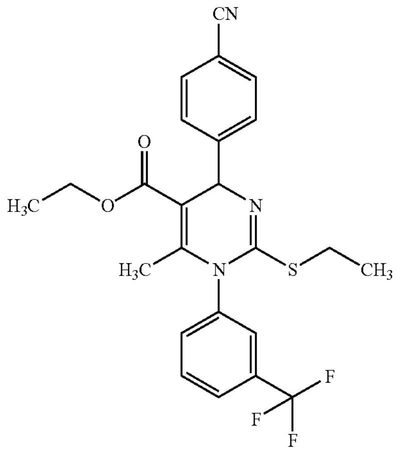

Ethyl 4-(4-cyanophenyl)-6-methyl-2-thioxo-1-[3-(trifluoromethyl)phenyl]-1,2,3,4-tetrahydro-5-pyrimidinecarboxylate (Example 3; 100 mg, 0.22 mmol), iodoethane (38.5 mg, 0.25 mmol) and potassium carbonate (34.1 mg, 0.25 mmol) are dissolved in 3 ml acetone and stirred at room temperature overnight. The solvent is removed in vacuo and the product is purified via preparative HPLC (RP18-column; eluent: acetonitrile-water, gradient 10:90 to 90:10).

Yield: 62 mg (58% of th.) LC-MS (method 2): $R_t$=4.67 min. MS (ESIpos): m/z=474 $(M+H)^+$ $^1$H-NMR (200 MHz, DMSO-$d_6$): δ=7.85 (d, 2H); 7.68-7.94 (m, 4H); 7.60 (d, 2H); 5.75 (s, 1H); 4.03 (q, 2H); 2.74 (m, 2H); 2.01 (s, 3H); 1.11 (t, 3H); 1.01 (t, 3H) ppm.

Example 10

Ethyl 4-(4-cyanophenyl)-6-methyl-2-(propylsulfanyl)-1-[3-trifluoromethyl)phenyl]-1,4dihydro-5-pyrimdinecarboxylate

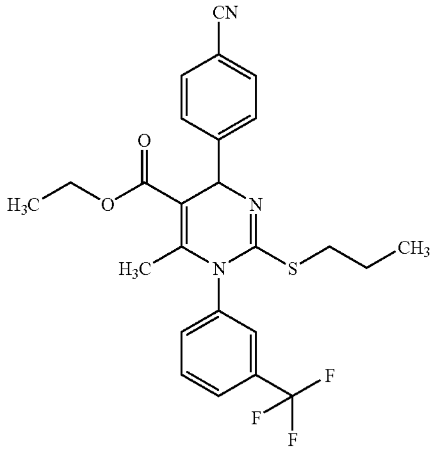

Ethyl 4-(4-cyanophenyl)-6-methyl-2-thioxo-1-[3-(trifluoromethyl)phenyl]-1,2,3,4-tetrahydro-5-pyrimidinecarboxylate (Example 3; 100 mg, 0.22 mmol), 1-iodopropane (42.0 mg, 0.25 mmol) and potassium carbonate (34.1 mg, 0.25 mmol) are dissolved in 3 ml acetone and stirred at room temperature overnight. The solvent is removed in vacuo and the product is purified via preparative HPLC (RP18-column; eluent: acetonitrile-water, gradient 10:90 to 90:10).

Yield: 45 mg (41% of th.) LC-MS (method 3): $R_t$=4.45 min. MS (ESIpos): m/z=488 $(M+H)^+$.

Example 11

Ethyl 4-(4-cyanophenyl)methyl-2-(butylsulfanyl)-1-[3-(trifluoromethyl)phenyl]-1,4-dihydro-5-pyrimidinecarboxylate

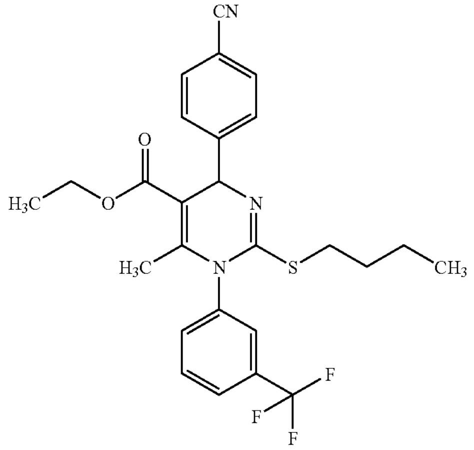

Ethyl 4-(4cyanophenyl)-6-methyl-2-thioxo-1-[3-(trifluoromethyl)phenyl]-1,2,3,4-tetrahydro-5-pyrimidinecarboxylate (Example 3; 100 mg, 0.22 mmol), 1-iodobutane (45.0 mg, 0.25 mmol) and potassium carbonate (34.1 mg, 0.25 mmol) are dissolved in 3 ml acetone and stirred at room temperature overnight. The solvent is removed in vacuo and the product is purified via preparative HPLC (RP18-column; eluent: acetonitrile-water, gradient 10:90 to 90:10).

Yield: 53 mg (47% of th.) LC-MS (method 3): $R_t$=4.58 min. MS (ESIpos): m/z=402 $(M+H)^+$.

Example 12

Ethyl 4-(4-cyanophenyl)-6-methyl-2-[(4-pyridinylmethyl)sulfanyl]-1-[3-(trifluoro-methyl)phenyl]-1,4-dihydro-5-pyrimidinecarboxylate

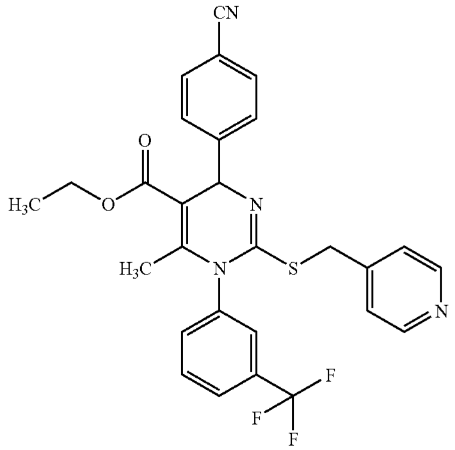

Ethyl 4-(4-cyanophenyl)-6-methyl-2-thioxo-1-[3-(trifluoromethyl)phenyl]-1,2,3,4-tetrahydro-5-pyrimidinecarboxylate (Example 3; 100 mg, 0.22 mmol), 4-(bromo-methyl) pyridine hydrobromide (62.5 mg, 0.25 mmol), N,N,N-tributyl-1-butan-aminium iodide (7 mg, 0.03 mmol) and potassium carbonate (65.2 mg, 0.47 mmol) are dissolved in 3 ml acetone and stirred at room temperature overnight. The solvent is removed in vacuo and the product is purified via preparative HPLC (RP18-column; eluent: acetonitrile-water, gradient 10:90 to 90:10).

Yield: 34 mg (28% of th.) LC-MS (method 3): $R_t$=3.92 min. MS (ESIpos): m/z=537 $(M+H)^{+1}$H-NMR (200 MHz, DMSO-$d_6$): δ=8.34 (m, 2H); 7.89 (m, 2H); 7.82 (d, 2H); 7.72 (m, 2H); 7.57 (d, 2H); 7.53 (m, 1H); 7.13 (dd, 1H); 5.78 (s,1H); 3.94-4.14 (m, 4H); 2.00 (s, 3H); 1.10 (t, 3H) ppm.

Example 13

Ethyl 4-(4-cyanophenyl)-6-methyl-2-[(3-pyridinylmethyl)sulfanyl]-1-[3-(trifluoro-methyl)phenyl]-1,4-dihydro-5-pyrimidinecarboxylate

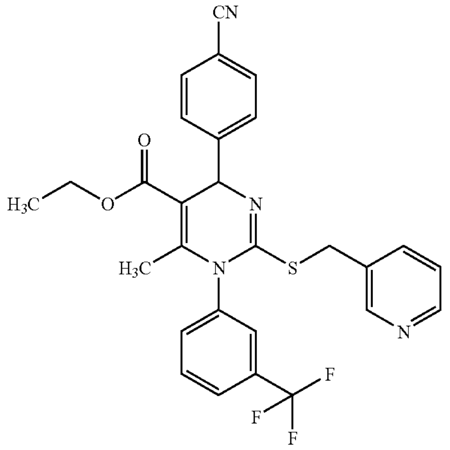

Ethyl 4-(4-cyanophenyl)-6-methyl-2-thioxo-1-[3-(trifluoromethyl)phenyl]-1,2,3,4-tetrahydro-5-pyrimidinecarboxylate (Example 3; 100 mg, 0.22 mmol), 3-(chloro-methyl) pyridine hydrochloride (40.5 mg, 0.25 mmol), N,N,N-tributyl-1-butan-aminium iodide (7 mg, 0.03 mmol) and potassium carbonate (65.2 mg, 0.47 mmol) are dissolved in 3 ml acetone and stirred at room temperature overnight. The solvent is removed in vacuo and the product is purified via preparative HPLC (RP18-column; eluent: acetonitrile-water, gradient 10:90 to 90:10).

Yield: 25 mg (21% of th.) LC-MS (method 2): $R_t$=3.93 min. MS (ESIpos): m/z=537 $(M+H)^+$.

Example 14

Ethyl 4-(4-cyanophenyl)-2-{[2-(diethylamino)ethyl] sulfanyl}-6-methyl-1-[3-(tri-fluoromethyl)phenyl]-1, 4dihydro-5-pyrimidinecarboxylate

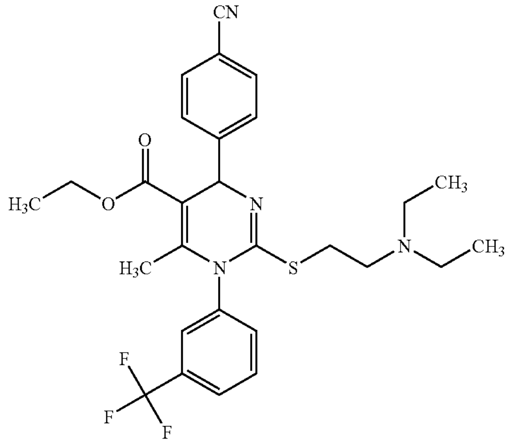

Ethyl 4-(4-cyanophenyl)-6-methyl-2-thioxo-1-[3-(trifluoromethyl)phenyl]-1,2,3,4-tetrahydro-5-pyrimidinecarboxylate (Example 3; 100 mg, 0.22 mmol), N-(2-bromo-ethyl)-N, N-diethylamine hydrobromide (64.5 mg, 0.25 mmol), N,N, N-tributyl-1-butanaminium iodide (7 mg, 0.03 mmol) and potassium carbonate (65.2 mg, 0.47 mmol) are dissolved in 3 ml acetone and stirred at room temperature overnight. The solvent is removed in vacuo and the product is purified via preparative HPLC (RP18-column; eluent: acetonitrile-water, gradient 10:90 to 90:10).

Yield: 15 mg (12% of th.) LC-MS (method 2): $R_t$=3.17 min. MS (ESIpos): m/z=545 $(M+H)^+$.

Example 15

Ethyl 4-(4cyanophenyl)2-[(1H-imidazol-2-ylmethyl) sulfanyl]-6-methyl-1-[3-(tri-fluoromethyl)phenyl]-1, 4-dihydro-5-pyrimidinecarboxylate

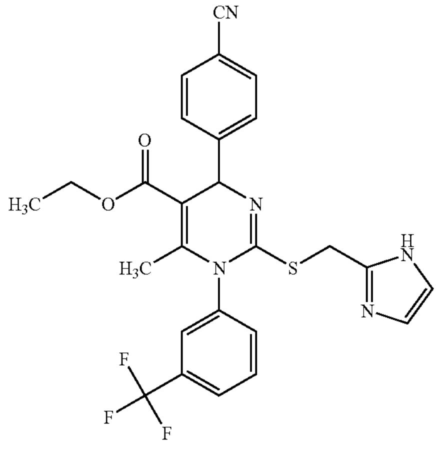

Ethyl 4-(4-cyanophenyl)-6-methyl-2-thioxo-1-[3-(trifluoromethyl)phenyl]-1,2,3,4-tetrahydro-5-pyrimidinecarboxylate (Example 3; 100 mg, 0.22 mmol), 2-(bromo-methyl)-1H-imidazole hydrobromide (64.5 mg, 0.25 mmol), N,N,N-tributyl-1-butan-aminium iodide (7 mg, 0.03 mmol) and potassium carbonate (65.2 mg, 0.47 mmol) are dissolved in 3 ml acetone and stirred at room temperature overnight. The solvent is removed by distillation in vacuo and the product is purified via preparative HPLC (RP18-column; eluent: acetonitrile-water, gradient 10:90 to 90:10).

Yield: 13 mg (11% of th.) LC-MS (method 3): $R_t$=3.74 min. MS (ESIpos): m/z=526 $(M+H)^+$.

Example 16

2-Cyanoethyl 4-(4-cyanophenyl)-6-methyl-2-thioxo-1-[3-(trifluoromethyl)phenyl]-1,2,3,4-tetrahydro-5-pyrimidinecarboxylate

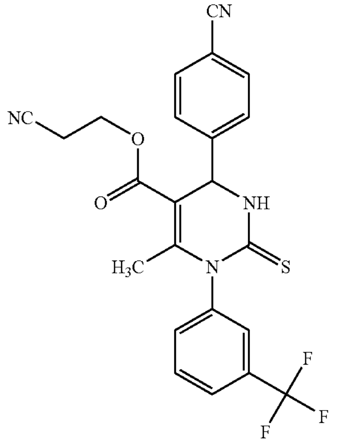

Under argon, trimethylsilyl polyphosphate (10.6 g) is dissolved in 75.7 ml absolute dioxane. To this solution are added 4-cyanobenzaldehyde (5.95 g, 45.4 mmol), 3-trifluoromethylphenyl thiourea (5 g, 22.7 mmol) and 2-cyanoethyl acetoacetate (6.4 g, 45.4 mmol). The reaction mixture is stirred at 80° C. for 3 hours. After evaporation of the dioxane solvent, the residue is dissolved in ethyl acetate and washed with saturated aqueous sodium bicarbonate solution, 38% sodium bisulfite solution and saturated sodium chloride solution. After drying with magnesium sulfate and evaporating off the solvent, the residue is dissolved in 15 ml methanol and purified by preparative HPLC (column: Kromasil 100 C 185 μm, 30 mm×150 mm; precolumn: Gromsil ODS 4 HE 15 μm, 10 mm×20 mm; flow rate: 66 ml/min; solvent A: acetonitrile, solvent B: water; gradient: 0 min 10% A, 3 min 10% A, 11 min 90% A, 13 min 90% A, 13.2 min 10% A, 15 min 10% A; wavelength: 220 nm; injection volume: approx. 2000 μl; number of injections: 12). The product containing fractions are combined and concentrated in vacuo.

Yield: 7.73 g (72.3% of th.) MS(ESIpos): m/z=471 $(M+H)^{+1}$H-NMR (200 MHz, DMSO-$d_6$): δ=10.3 (d, 1H); 7.9 (d, 2H); 7.4-7.8 (m, 6H); 5.4 (d, 1H); 4.25 (m, 2H); 2.9 (tr, 2H); 2.1 (s, 3H) ppm.

In analogy to the procedure of Example 16, the following compounds are prepared:

| Ex.-No. | Structure | Starting materials | Yield [%] | Mass $[M + H]^+$ |
|---|---|---|---|---|
| 17 | 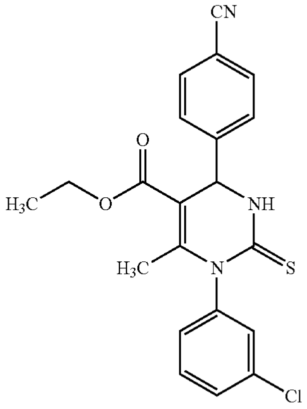 | 4-cyano-benzaldehyde; 3-chlorophenyl thiourea; ethyl acetoacetate | 71 | 412 |
| 18 | 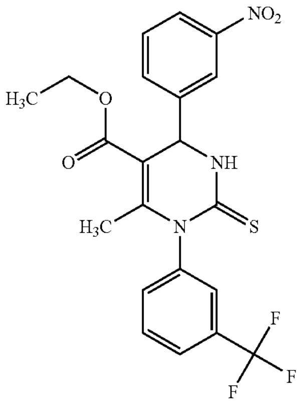 | 3-nitro-benzaldehyde; 3-trifluoro-methylphenyl thiourea; ethyl acetoacetate | 74 | 466 |

Example 19

4-(4-Cyanophenyl)-6-methyl-2-thioxo-1-[3-(trifluoromethyl)phenyl]-1,2,3,4-tetra-hydropyrimidine-5-carboxylic acid

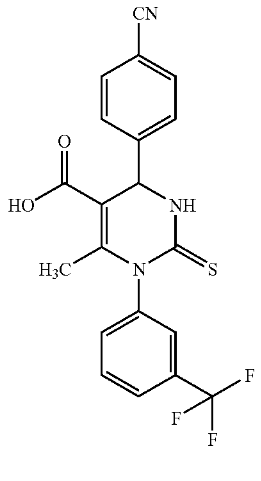

2-Cyanoethyl 4-(4-cyanophenyl)-6-methyl-2-thioxo-1-[3-(trifluoromethyl)phenyl]-1,2,3,4-tetrahydro-5-pyrimidinecarboxylate (Example 16; 47 mg, 0.1 mmol) is dissolved in 0.5 ml dioxane. After addition of 1,8-diazabicyclo[5.4.0]undec-7-ene (15 μl, 15 mg, 0.1 mmol), the reaction mixture is stirred at room temperature for 3 hours. The reaction mixture is diluted with 1 N hydrochloric acid and extracted with ethyl acetate. After drying with magnesium sulfate and evaporating off the solvent, the residue is purified by preparative HPLC (column: Nucleosil 100-5 C 18 Nautilus 20 mm×50 mm, 5 μm; solvent A: acetonitrile, solvent B: water+0.1% formic acid; flow rate: 25 ml/min; gradient: 0 min 10% A, 2 min 10% A, 6 min 90% A, 7 min 90% A, 7.1 min 10% A, 8 min 10% A; wavelength: 220 nm; injection volume: approx. 550 μl; number of injections: 1). The product containing fractions are combined and concentrated in vacuo.

Yield: 7.73 g (72.3 % of th.) MS (EI): m/z=417 $(M+H)^+$ LC-MS (method 1): $R_t$=4.2 min. $^1$H-NMR (200 MHz, DMSO-$d_6$): δ=12.8 (broad s, 1H); 10.15 (d, 1H); 7.9 (d, 2H); 7.4-7.8 (m, 6H); 5.4 (d, 1H); 2.1 (s, 3H) ppm.

Example 20

4-{5-(1-Hydroxyethyl)-6-methyl-2-thioxo-1-[3-(trifluoromethyl)phenyl]-1,2,3,4-tetrahydro-4-pyrimidinyl}benzonitrile

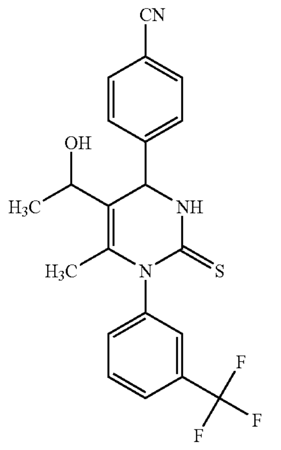

4-{5-Acetyl-6-methyl-2-thioxo-1-[3-(trifluoromethyl)phenyl]-1,2,3,4-tetrahydro-4-pyrimidinyl}benzonitrile (Example 1; 100 mg, 0.24 mmol) is dissolved in 3 ml methanol, and sodium borohydride (10 mg, 0.26 mmol) is added. After stirring at room temperature for 1 h, the crude mixture is purified via preparative HPLC (RP18-column; eluent: acetonitrile-water, gradient 10:90 to 90:10) to give the product as a 1.6:1-mixture of the two diastereomers.

Yield: 86 mg (86% of th.) LC-MS (method 4): $R_t$=4.10 min. MS (ESIpos): m/z=418 $(M+H)^+$.

Example 21

Ethyl 4-(4-cyano-2-methylphenyl)-6-methyl-2-thioxo-1-[3-(trifluoromethyl)phenyl]-1,2,3,4-tetrahydro-5-pyrimidinecarboxylate

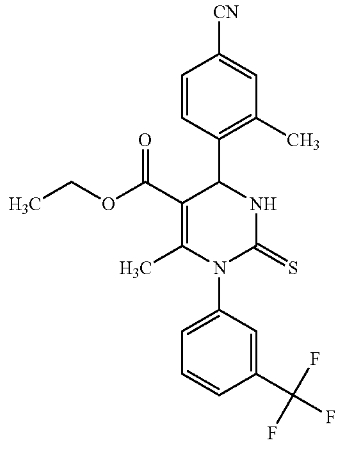

4-Cyano-2-methylbenzaldehyde (200 mg, 1.38 mmol), 3-trifluoromethylphenyl thiourea (276 mg, 1.25 mmol), ethyl 3-oxobutanoate (179 mg, 1.38 mmol) and trimethylsilyl polyphosphate (225 mg) in 5 ml THF are stirred overnight at reflux temperature. The reaction mixture is cooled to room temperature, and after addition of 20 ml 0.5 M hydrochloric acid the aqueous phase is extracted with ethyl acetate (2×20 ml). The combined organic layers are washed with saturated aqueous sodium carbonate solution and dried with sodium sulfate. The solvent is removed in vacuo and the crude product is purified via preparative HPLC (RP18-column; eluent: aceto-nitrile-water, gradient 10:90 to 90:10).

Yield: 320 mg (56% of th.) LC-MS (method 5): $R_t$=4.32 min. MS (ESIpos): m/z=460 $(+H)^{+1}$H-NMR (200 MHz, DMSO-$d_6$): δ=10.09 (d, 1H); 7.63-7.86 (m, 7H); 5.61 (d, 1H); 3.97 (q, 2H); 2.56 (s, 3); 2.08 (s, 3H); 1.00 (t, 3H) ppm.

Example 22

4-{5-Acetyl-6-methyl-3-propionyl-2-thioxo-1-[3-(trifluoromethyl)phenyl]-1,2,3,4-tetrahydro-4-pyrimidinyl}benzonitrile

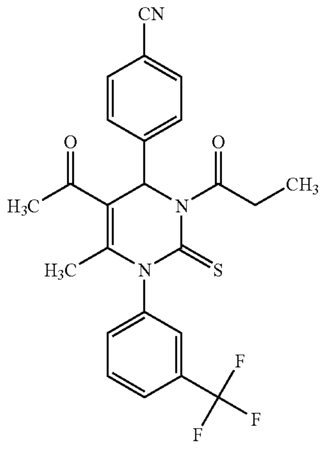

4-{5-Acetyl-6-methyl-2-thioxo-1-[3-(trifluoromethyl)phenyl]-1,2,3,4-tetrahydro-4-pyrimidinyl}benzonitrile (Example 1; 100 mg, 0.24 mmol) is dissolved in 3 ml THF. After addition of pyridine (21 mg, 0.26 mmol) and propanoyl chloride (22 mg, 0.24 mmol), the reaction mixture is stirred at room temperature overnight and is then quenched with 10 ml water. After extraction with ethyl acetate (2×10 ml), the organic layer is dried with sodium sulfate, and the crude product is purified via flash chromatography on silica gel using a gradient of cyclohexane/ethyl acetate.

Yield: 78 mg (69% of th.) LC-MS (method 6): $R_t$=4.23 min. MS (ESIpos): m/z=472 $(M+H)^{+1}$H-NMR (200 MHz, DMSO-$d_6$): δ=7.44-7.97 (m, 8H); 6.66 (s, 1H); 3.28 (m, 1H); 2.87 (m, 1H); 2.45 (s, 3H); 2.09 (s, 3H); 1.17 (t, 3H) ppm.

In analogy to the procedure of Example 22, the following compounds are prepared:
| Ex.-No. | Structure | Starting materials | Yield [%] | $R_t$ [min] (method) | Mass $[M + H]^+$ |
| --- | --- | --- | --- | --- | --- |
| 23 | 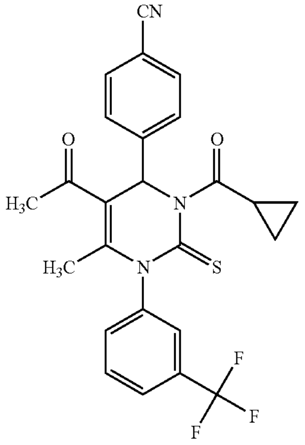 | Example 1; cyclopropyl carbonyl chloride | 74 | 4.22 (6) | 484 |
| 24 | 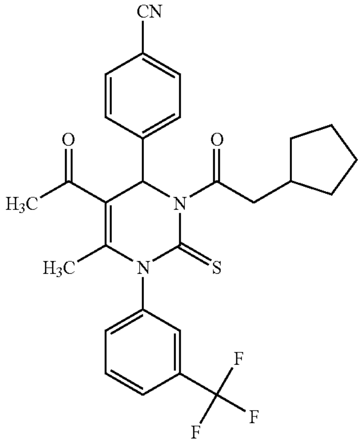 | Example 1; cyclopentyl-acetyl chloride | 74 | 4.73 (6) | 526 |
| 25 | 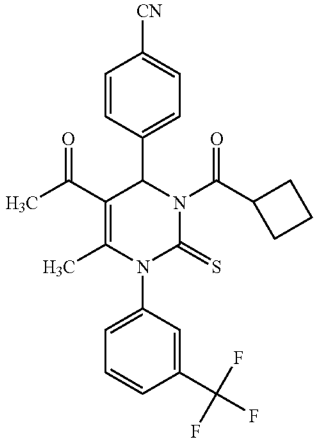 | Example 1; cyclobutyl carbonyl chloride | 42 | 4.44 (6) | 498 |

-continued
| Ex.-No. | Structure | Starting materials | Yield [%] | $R_t$ [min] (method) | Mass $[M + H]^+$ |
|---|---|---|---|---|---|
| 26 | 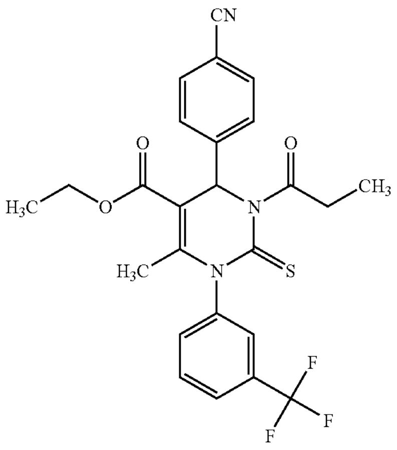 | Example 3; propanoyl chloride | 68 | 4.30 (7) | 502 |
| 27 | 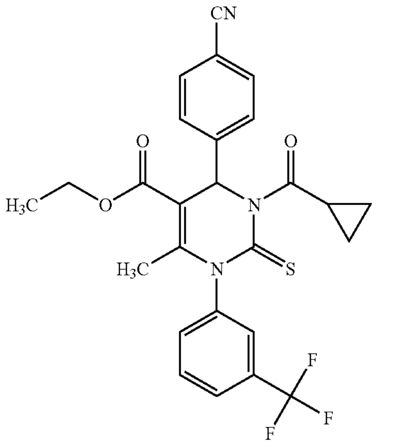 | Example 3; cyclopropyl carbonyl chloride | 70 | 4.30 (7) | 514 |
| 28 | 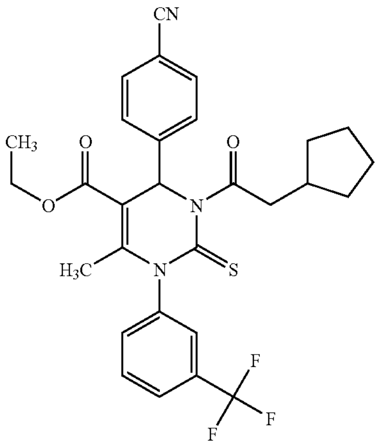 | Example 3; cyclopentyl acetyl chloride | 61 | 4.60 (7) | 556 |

-continued

| Ex.-No. | Structure | Starting materials | Yield [%] | $R_t$ [min] (method) | Mass $[M + H]^+$ |
|---|---|---|---|---|---|
| 29 | 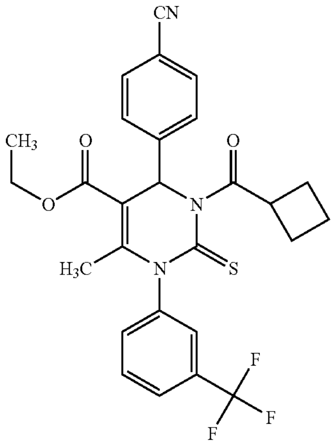 | Example 3; cyclobutyl carbonyl chloride | 59 | 4.40 (7) | 528 |

Example 30

4-{5-Acetyl-6-methyl-2-(methylsulfanyl)-1-[3-(trifluoromethyl)phenyl]-1,4-dihydro-4-pyrimidinyl}benzonitrile

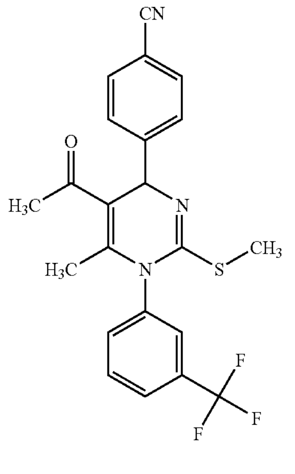

4-{5-Acetyl-6-methyl-2-thioxo-1-[3-(trifluoromethyl)phenyl]-1,2,3,4-tetrahydro-4-pyrimidinyl}benzonitrile (example 1; 100 mg, 0.24 mmol), 1-iodomethane (38.0 mg, 0.27 mmol) and potassium carbonate (34.1 mg, 0.25 mmol) are dissolved in 3 ml acetone and stirred at room temperature overnight. The solvent is removed in vacuo and the crude product is purified via preparative HPLC (RP1 8-column; eluent: aceto-nitrile-water, gradient 10:90 to 90:10).

Yield: 67 mg (65% of th.) LC-MS (method 4): $R_t$=4.30 min. 5 MS (ESIpos): m/z=430 $(M+H)^{+1}$H-NMR (200 MHz, DMSO-$d_6$): δ=7.55-7.96 (m, 8H); 5.85 (s, 1H); 2.19 (s, 3H); 2.16 (s, 3H); 1.98 (s, 3H) ppm.

Example 31

Ethyl 4-(4-cyano-2-methylphenyl)-6-methyl-2-(methylsulfanyl)-1-[3-(trifluoro-methyl)phenyl]-1,4-dihydro-5-pyrimidinecarboxylate

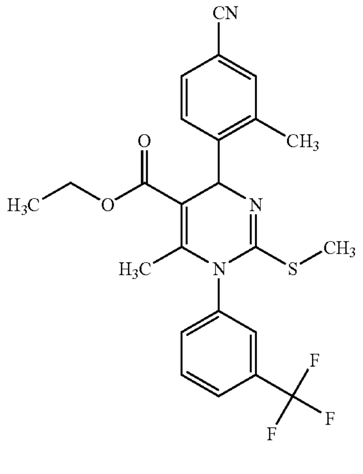

Ethyl 4-(4-cyano-2-methylphenyl)-6-methyl-2-thioxo-1-[3-(trifluoromethyl)phenyl]-1,2,3,4-tetrahydro-5-pyrimidinecarboxylate (Example 21; 100 mg, 0.22 mmol), 1-iodomethane (34.0 mg, 0.24 mmol) and potassium carbonate (34.1 mg, 0.25 mmol) are dissolved in 3 ml acetone and stirred at room temperature overnight. The solvent is removed in vacuo and the crude product is purified via preparative HPLC (RP18-column; eluent: acetonitrile-water, gradient 10:90 to 90:10).

Yield: 78 mg (76% of th.) LC-MS (method 3): $R_t$=4.70 min. MS (ESIpos): m/z=474 $(M+H)^+$.

Example 32

Acetic acid 2-[5-acetyl(4-cyanophenyl)-6-methyl-1-[3-(trifluoromethyl)phenyl]-1,4-dihydropyrimidine-2-ylsulfanyl]-ethyl ester

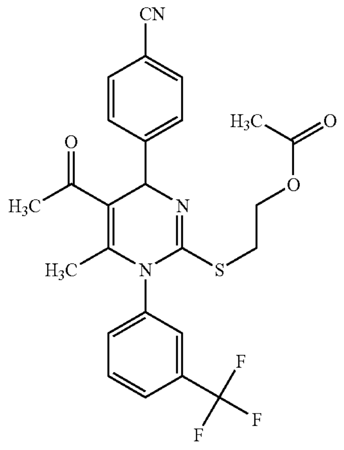

To a solution of 2-bromoethyl acetate (37.6 mg, 0.23 mmol) in 500 μl DMF are added potassium carbonate (82.9 mg, 0.6 mmol) and 4-{5-acetyl-6-methyl-2-thioxo-1-[3-(trifluoromethyl)phenyl]-1,2,3,4-tetrahydro-4-pyrimidinyl}benzonitrile (Example 1; 62.3 mg, 0.15 mmol). The reaction mixture is shaken for 15 hours, filtered and purified by preparative HPLC (column: Nucleosil 100-5 C 18 Nautilus 20 mm×50 mm, 5 μm; solvent A: acetonitrile, solvent B: water+0.1% formic acid; flow rate: 25 ml/min; gradient: 0 min 10% A, 2 min 10% A, 6 min 90% A, 7 min 90% A, 7.1 min 10% A, 8 nm 10% A; wavelength: 220 um; injection volume: approx. 550 μl; number of injections: 1). The product containing fractions are combined and concentrated in vacuo.

Yield: 0.6 mg (0.8% of th.) LC-MS (method 3): $R_t$=4.38 min. MS (ESIpos): m/z=502 $(M+H)^+$.

In analogy to the procedure of Example 32, the following compounds are prepared:

| Ex.-No. | Structure | Starting materials | Yield [%] | $R_t$ [min] (method) | Mass $[M + H]^+$ |
|---|---|---|---|---|---|
| 33 | 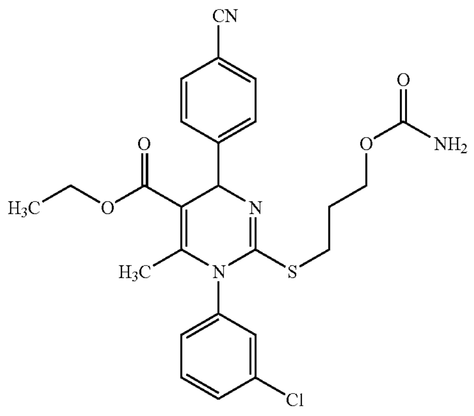 | Example 17; carbamic acid 3-bromo-propyl ester | 20.3 | 3.95 (7) | 513 |
| 34 | 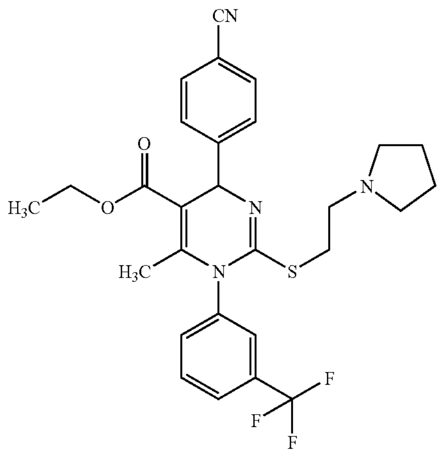 | Example 3; 1-(2-chloro-ethyl)-pyrrolidine hydrochloride | 3.3 | 3.19 (7) | 543 |

-continued
| Ex.-No. | Structure | Starting materials | Yield [%] | $R_t$ [min] (method) | Mass $[M + H]^+$ |
|---|---|---|---|---|---|
| 35 | 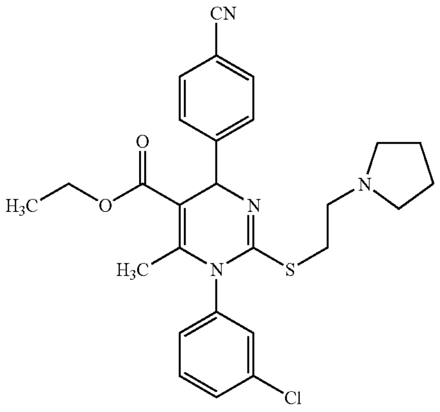 | Example 17; 1-(2-chloro-ethyl)-pyrrolidine hydrochloride | 3.8 | 3.16 (7) | 509 |
| 36 | 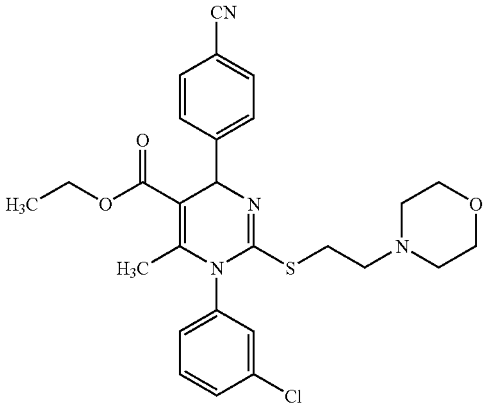 | Example 17; 4-(2-chloro-ethyl)-morpholine hydrochloride | 3.8 | 3.14 (7) | 525 |
| 37 | 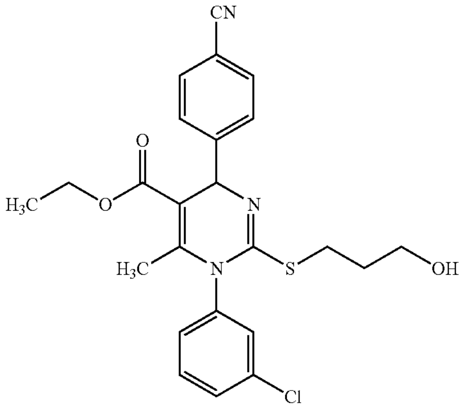 | Example 17; 3-bromo-propan-1-ol | 34.5 | 4.02 (8) | 470 |

-continued
| Ex.-No. | Structure | Starting materials | Yield [%] | $R_t$ [min] (method) | Mass $[M + H]^+$ |
|---|---|---|---|---|---|
| 38 | 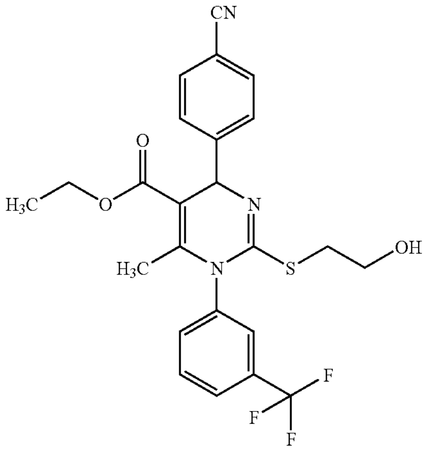 | Example 3; 2-bromo-ethanol | 25.9 | 4.3 (7) | 474 |
| 39 | 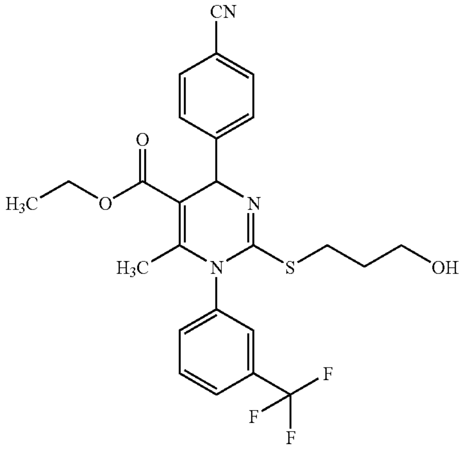 | Example 3; 3-bromo-propan-1-ol | 18.5 | 4.29 (3) | 504 |
| 40 | 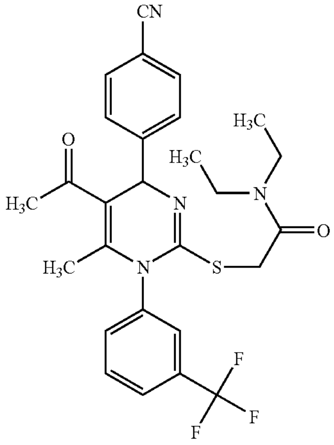 | Example 1; 2-bromo-N,N-diethyl-acetamide | 37.8 | 4.24 (3) | 529 |

-continued
| Ex.-No. | Structure | Starting materials | Yield [%] | $R_t$ [min] (method) | Mass $[M + H]^+$ |
|---|---|---|---|---|---|
| 41 | 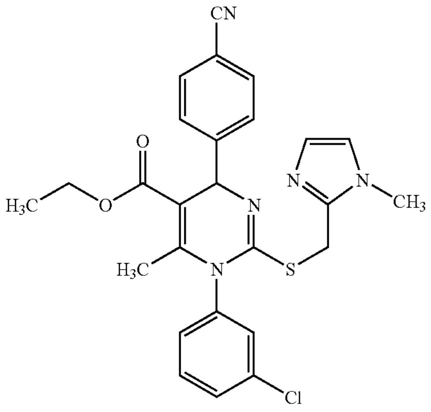 | Example 17; 2-chloro-methyl-1-methyl-1H-imidazole hydrochloride | 54.1 | 3.59 (3) | 506 |
| 42 | 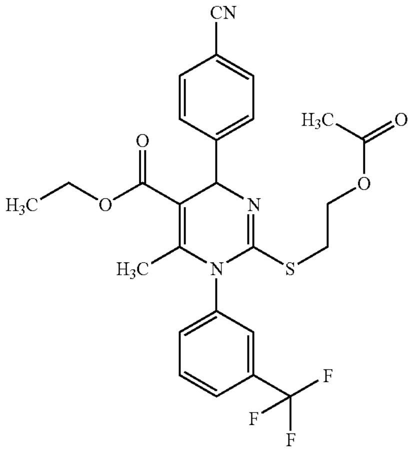 | Example 3; 2-bromoethyl acetate | 16.3 | 4.49 (3) | 532 |
| 43 | 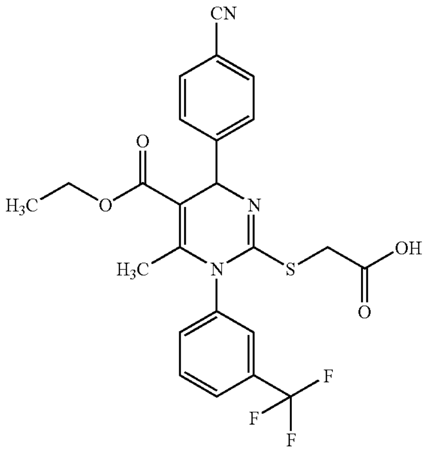 | Example 3; bromoacetic acid | 26.5 | 3.94 (7) | 504 |

-continued
| Ex.-No. | Structure | Starting materials | Yield [%] | $R_t$ [min] (method) | Mass $[M + H]^+$ |
|---|---|---|---|---|---|
| 44 | 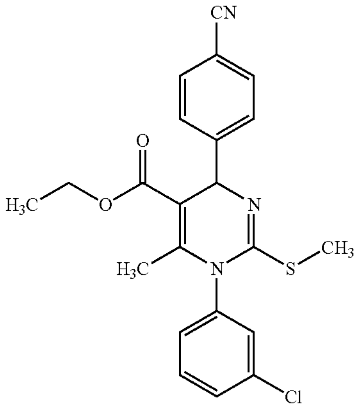 | Example 17; iodomethane | 37.6 | 4.44 (3) | 426 |
| 45 | 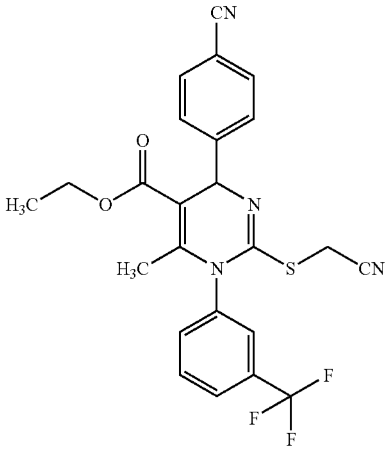 | Example 3; bromo-acetonitrile | 49.5 | 3.71 (3) | 485 |
| 46 | 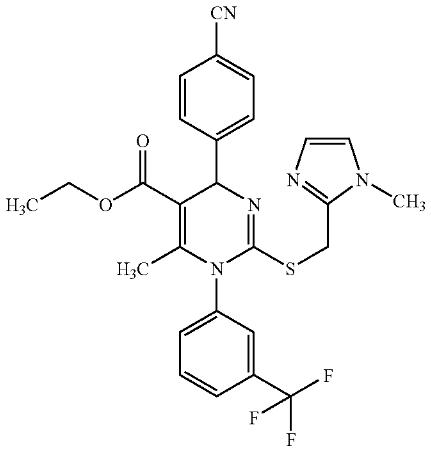 | Example 3; 2-chloro-methyl-1-methyl-1H-imidazole hydrochloride | 40.8 | 3.13 (7) | 540 |

-continued
| Ex.-No. | Structure | Starting materials | Yield [%] | $R_t$ [min] (method) | Mass $[M+H]^+$ |
|---|---|---|---|---|---|
| 47 | 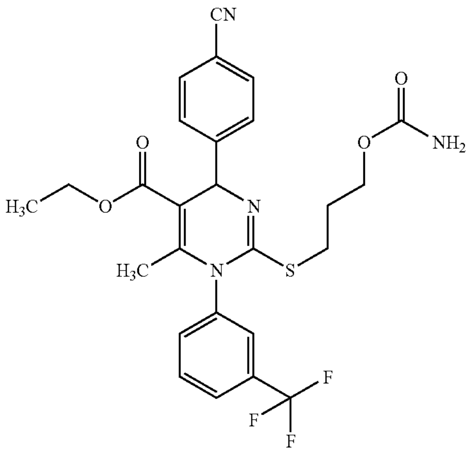 | Example 3; carbamic acid 3-bromo-propyl ester | 14.6 | 3.94 (7) | 547 |
| 48 | 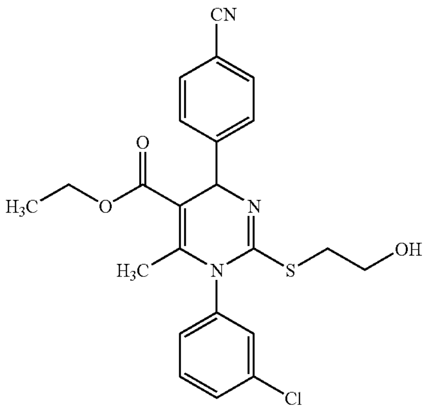 | Example 17; 2-bromo-ethanol | 33.6 | 4.21 (3) | 456 |
| 49 | 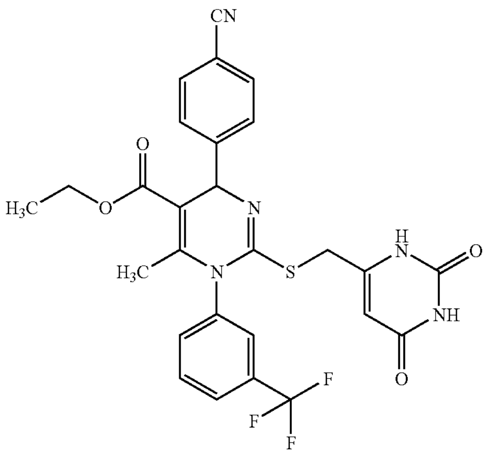 | Example 3; 6-chloro-methyl-1H-pyrimidine-2,4-dione | 53.8 | 3.75 (7) | 570 |

-continued
| Ex.-No. | Structure | Starting materials | Yield [%] | $R_t$ [min] (method) | Mass $[M + H]^+$ |
|---|---|---|---|---|---|
| 50 | 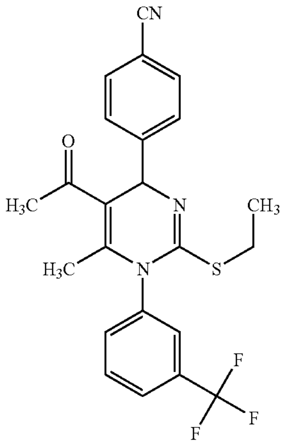 | Example 1; iodoethane | 24.0 | 4.05 (7) | 444 |
| 51 | 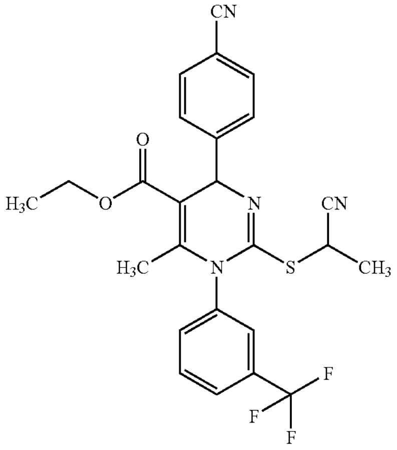 | Example 3; 2-bromo-propionitrile | 13.3 | 3.75 (3) | 499 |
| 52 | 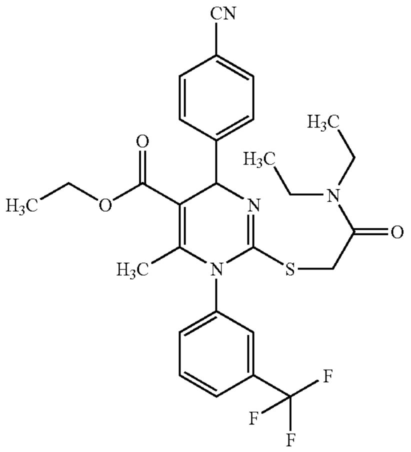 | Example 3; 2-bromo-N,N-diethyl-acetamide | 51.3 | 4.45 (3) | 559 |

-continued
| Ex.-No. | Structure | Starting materials | Yield [%] | $R_t$ [min] (method) | Mass $[M + H]^+$ |
|---|---|---|---|---|---|
| 53 | 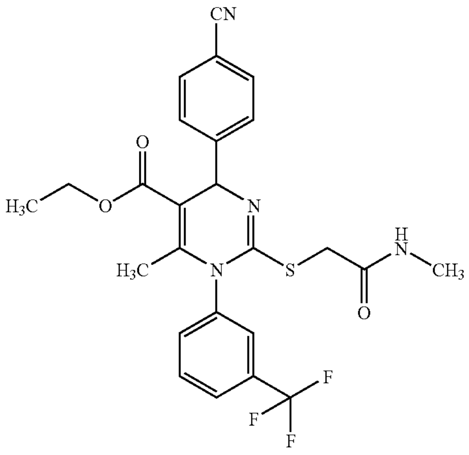 | Example 3; 2-bromo-N-methyl-acetamide | 59.4 | 3.9 (7) | 517 |
| 54 | 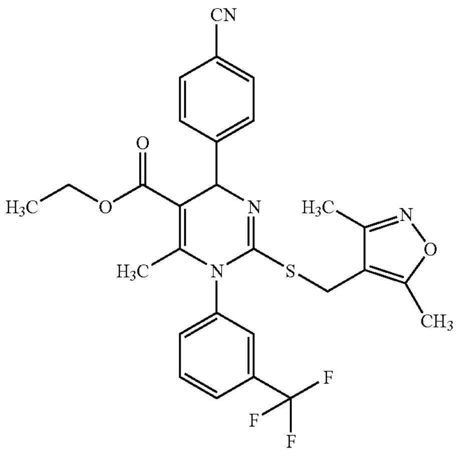 | Example 3; 4-chloro-methyl-3,5-dimethyl-isoxazole | 60.1 | 4.22 (7) | 555 |
| 55 | 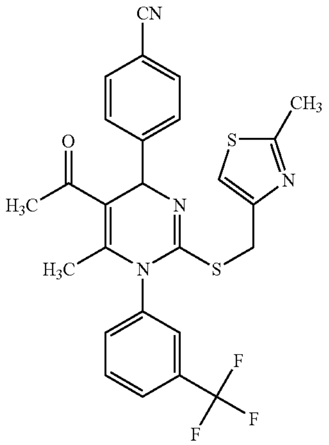 | Example 1; 4-chloro-methyl-2-methyl-thiazole hydrochloride | 5.4 | 3.96 (7) | 527 |

-continued

| Ex.-No. | Structure | Starting materials | Yield [%] | $R_t$ [min] (method) | Mass $[M + H]^+$ |
|---|---|---|---|---|---|
| 56 | 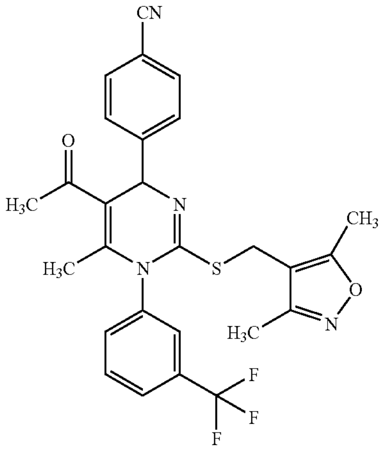 | Example 1; 4-chloro-methyl-3,5-dimethyl-isoxazole | 21.6 | 4.02 (7) | 525 |

Example 57

4-(4-Cyanophenyl)-6-methyl-2-(methylsulfanyl)-1-[3-(trifluoromethyl)phenyl]-1,4-dihydro-5-pyrimidinecarboxylic acid

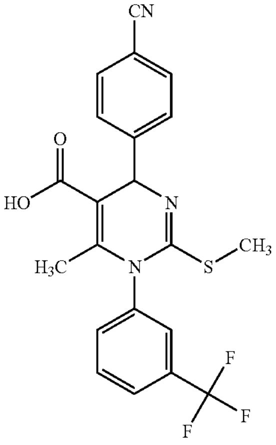

Methyl 4-(4-cyanophenyl)-6-methyl-2-(methylsulfanyl)-1-[3-(trifluoromethyl)-phenyl]-1,4-dihydro-5-pyrimidinecarboxylate (Example 8; 9.51 g, 21.4 mmol) is dissolved in 175 ml THF/ethanol/water (10:5:1). Potassium hydroxide (3.59 g, 64.1 mmol) is added, and the reaction mixture is stirred overnight. The reaction mixture is diluted with 100 ml of water, and the aqueous phase is washed with diethyl ether. The resulting aqueous phase is acidified to pH 1 with hydrochloric acid, and the resulting precipitate is filtered off, dissolved in ethyl acetate and washed with water. After drying with sodium sulfate, the solvent is removed in vacuo to give the product.

Yield: 655 mg (7% of th.) LC-MS (method 5): $R_t$=3.77 min. MS (ESIpos): m/z=432 $(M+H)^+$ $^1$H-NMR (200 MHz, DMSO-$d_6$): δ=12.32 (broad s, 1H); 7.52-7.98 (m, 8H); 5.75 (s, 1H); 2.15 (s, 3H); 2.02 (s, 3H) ppm.

Example 58

2-(Diethylamino)ethyl 4-(4-cyanophenyl)-6-methyl-2-(methylsulfanyl)-1-[3-(tri-fluoromethyl)phenyl]-1,4-dihydro-5-pyrimidinecarboxylate

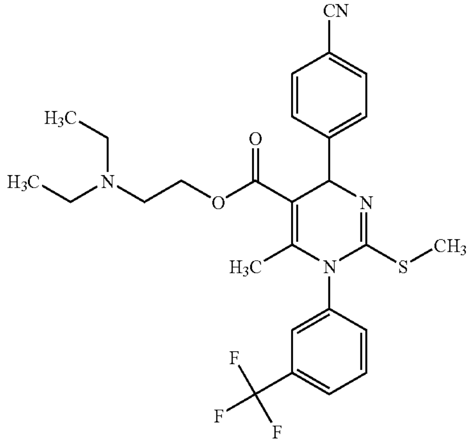

4-(4-Cyanophenyl)-6-methyl-2-(methylsulfanyl)-1-[3-(trifluoromethyl)phenyl]-1,4-dihydro-5-pyrimidinecarboxylic acid (Example 57; 100 mg, 0.23 mmol) is dissolved in 3 ml acetone. Potassium carbonate (67 mg, 0.49 mmol), N-(2-bromoethyl)-N,N-diethylamine hydrobromide (67 mg, 0.25 mmol) and N,N,N-tributyl-1-butan-aminium iodide (~5 mg) are added, and the reaction mixture is stirred at room temperature for 4 hours. The solvent is removed in vacuo, ethyl acetate is added and after extraction with 1 N sodium hydroxide solution, the organic layer is dried and the solvent is evaporated. The crude product is purified via preparative HPLC (RP18-column; eluent: acetonitrile-water, gradient 10:90 to 90:10).

Yield: 90 mg (73% of th.) LC-MS (method 5): $R_t$=3.00 min. MS (ESIpos): m/z=531 $(M+H)^+$ $^1$H-NMR (200 MHz, DMSO-$d_6$): δ=7.55-7.98 (m, 8H); 5.78 (s, 1H); 4.07 (t, 2H); 2.62 (t, 2H); 2.41-2.58 (m, 4H); 2.15 (s, 3H); 2.03 (s, 3H); 0.91 (t, 6H) ppm.

In analogy to the procedure of Example 58, the following compounds are prepared:
| Ex.-No. | Structure | Starting materials | Yield [%] | $R_t$ [min] (method) | Mass $[M+H]^+$ |
|---|---|---|---|---|---|
| 59 | 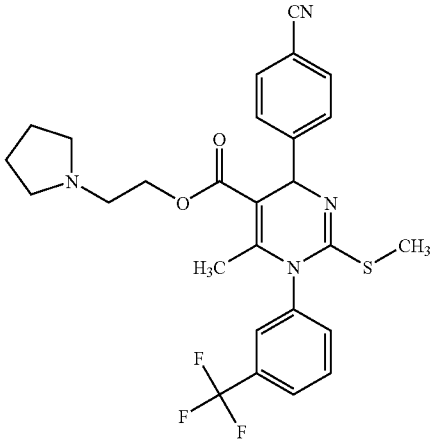 | Example 57; 1-(2-chloro-ethyl)-pyrrolidine hydrochloride | 43 | 3.80 (4) | 513 |
| 60 | 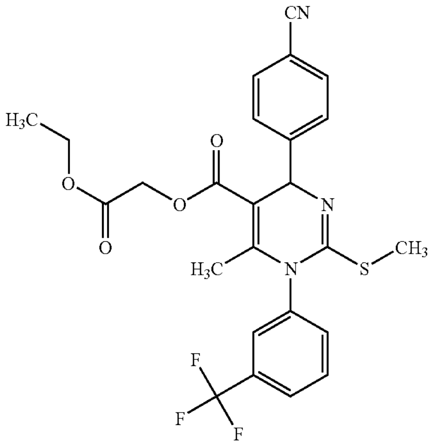 | Example 57; ethyl bromo-acetate | 42 | 4.50 (4) | 518 |
| 61 | 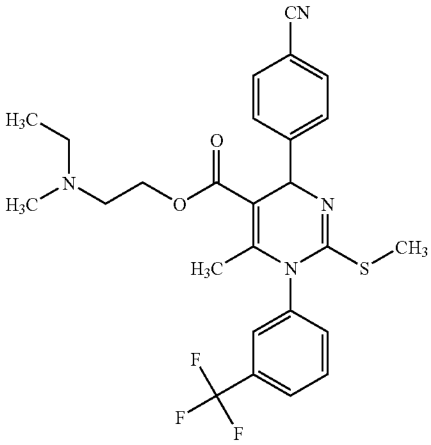 | Example 57; 2-chloro-N-ethyl-N-methyl-ethanamine hydrochloride | 48 | 3.70 (4) | 517 |

-continued

| Ex.-No. | Structure | Starting materials | Yield [%] | $R_t$ [min] (method) | Mass $[M + H]^+$ |
|---|---|---|---|---|---|
| 62 | 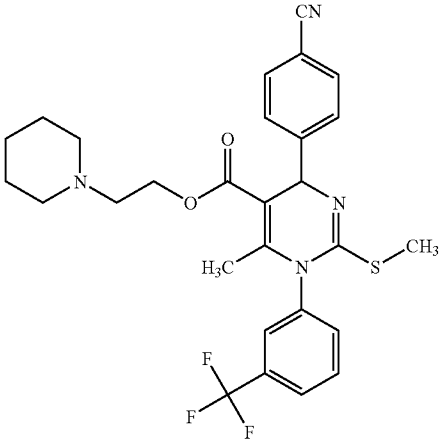 | Example 57; 1-(2-chloro-ethyl)-piperidine hydrochloride | 46 | 3.80 (4) | 543 |
| 63 | 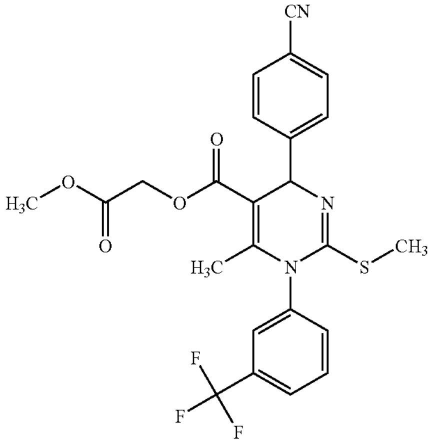 | Example 57; methyl chloroacetate | 71 | 4.10 (7) | 504 |

C. Operative Examples Relating to Pharmaceutical Compositions

The compounds according to the invention can be converted into pharmaceutical preparations as follows:

Tablet:

Composition:

100 mg of the compound of Example 1, 50 mg of lactose (monohydrate), 50 mg of maize starch (native), 10 mg of polyvinylpyrrolidone (PVP 25) (from BASF, Ludwigshafen, Germany) and 2 mg of magnesium stearate. Tablet weight 212 mg, diameter 8 mm, curvature radius 12 mm.

Preparation:

The mixture of active component, lactose and starch is granulated with a 5% solution (m/m) of the PVP in water. After drying, the granules are mixed with magnesium stearate for 5 min. This mixture is moulded using a customary tablet press (tablet format, see above). The moulding force applied is typically 15 kN.

Orally Administrable Suspension:

Composition:

1000 mg of the compound of Example 1, 1000 mg of ethanol (96%), 400 mg of Rhodigel (xanthan gum from FMC, Pennsylvania, USA) and 99 g of water.

A single dose of 100 mg of the compound according to the invention is provided by 10 ml of oral suspension.

Preparation:

The Rhodigel is suspended in ethanol and the active component is added to the suspension. The water is added with stirring. Stirring is continued for about 6 h until the swelling of the Rhodigel is complete.

We claim:

1. A compound of formula (I-A)

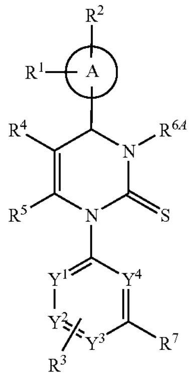

(I-A)

wherein

A represents a phenyl ring, $R^1$ represents hydrogen, or $C_1$-$C_6$-alkyl wherein $C_1$-$C_6$-alkyl can be further substituted with one to three identical or different radicals selected from the group consisting of halogen, hydroxy and $C_1$-$C_4$-alkoxy, $R^2$ represents cyano, $R^3$ represents hydrogen, $R^4$ represents $C_1$-$C_6$-alkyl, $C_1$-$C_6$-alkylcarbonyl, $C_1$-$C_6$-alkoxycarbonyl, hydroxy-carbonyl, aminocarbonyl, mono- or di-$C_1$-$C_4$-alkylaminocarbonyl, $C_6$-$C_{10}$-arylaminocarbonyl, heteroarylcarbonyl, heterocyclylcarbonyl, heteroaryl, heterocyclyl or cyano, wherein $C_1$-$C_6$-alkyl, $C_1$-$C_6$-alkylcarbonyl, $C_1$-$C_6$-alkoxycarbonyl, mono- and di-$C_1$-$C_4$-alkylaminocarbonyl can be further substituted with one to three identical or different radicals selected from the group consisting of $C_3$-$C_8$-cycloalkyl, hydroxy, $C_1$-$C_4$-alkoxy, $C_1$-$C_4$-alkoxycarbonyl, hydroxycarbonyl, aminocarbonyl, mono- and di-$C_1$-$C_4$-alkylaminocarbonyl, $C_1$-$C_4$-alkylcarbonylamino, amino, mono- and di-$C_1$-$C_4$-alkylamino, heteroaryl, heterocyclyl, tri-($C_1$-$C_6$-alkyl)-silyl and cyano, $R^5$ represents $C_1$-$C_4$-alkyl, $R^{6a}$ represents hydrogen, $C_1$-$C_6$-alkylcarbonyl, $C_3$-$C_8$-cycloalkylcarbonyl, wherein $C_1$-$C_6$-alkyl-carbonyl can be substituted with one to three identical or different radicals selected from the group consisting of $C_3$-$C_8$-cycloalkyl, hydroxy, $C_1$-$C_4$-alkoxy, amino, mono- and di-$C_1$-$C_4$-alkylamino, $R^7$ represents halogen, or $C_1$-$C_6$-alkyl, wherein $C_1$-$C_6$-alkyl can be further substituted with one to three identical or different radicals selected from the group consisting of halogen, hydroxy and $C_1$-$C_4$-alkoxy, and $Y^1$, $Y^2$, $Y^3$ and $Y^4$ each represent CH.

2. The compound of formula (I-A) according to claim 1, wherein

A represents a phenyl, ring, $R^1$ hydrogen, $C_1$-$C_6$-alkyl wherein $C_1$-$C_6$-alkyl can be further substituted with one to three identical or different radicals selected from the group consisting of halogen, hydroxy and $C_1$-$C_4$-alkoxy, $R^2$ represents cyano, $R^3$ represents hydrogen, $R^4$ represents $C_1$-$C_6$-alkylcarbonyl, $C_1$-$C_6$-alkoxycarbonyl, hydroxycarbonyl, amino-carbonyl, mono- or di-$C_1$-$C_4$-alkylaminocarbonyl, $C_6$-$C_{10}$-arylaminocarbonyl, heteroarylcarbonyl, heterocyclylcarbonyl, heteroaryl, heterocyclyl or cyano, wherein $C_1$-$C_6$-alkylcarbonyl, $C_1$-$C_6$-alkoxycarbonyl, mono- and di-$C_1$-$C_4$-alkylaminocarbonyl can be further substituted with one to three identical or different radicals selected from the group consisting of $C_3$-$C_8$-cycloalkyl, hydroxy, $C_1$-$C_4$-alkoxy, $C_1$-$C_4$-alkoxycarbonyl, hydroxycarbonyl, aminocarbonyl, mono- and di-$C_1$-$C_4$-alkylaminocarbonyl, $C_1$-$C_4$-alkylcarbonylamino, amino, mono- and di-$C_1$-$C_4$-alkylamino, heteroaryl, heterocyclyl and tri-($C_1$-$C_6$-alkyl)-silyl, $R^5$ represents $C_1$-$C_4$-alkyl, $R^{6a}$ represents hydrogen, $C_1$-$C_6$-alkylcarbonyl, $C_3$-$C_8$-cycloalkylcarbonyl, wherein $C_1$-$C_6$-alkyl-carbonyl, can be substituted with one to three identical or different radicals selected from the group consisting of $C_3$-$C_8$-cycloalkyl, hydroxy, $C_1$-$C_4$-alkoxy, amino, mono- and di-$C_1$-$C_4$-alkylamino, $R^7$ represents halogen, or $C_1$-$C_6$-alkyl, wherein $C_1$-$C_6$-alkyl can be further substituted with one to three identical or different radicals selected from the group consisting of halogen, hydroxy and $C_1$-$C_4$-alkoxy, and $Y^1$, $Y^2$, $Y^3$ and $Y^4$ each represent CH.

3. The compound of formula (I-A) according to claim 1, wherein

A represents a phenyl ring, $R^1$ represents hydrogen, methyl, ethyl, trifluoromethyl or trifluoromethoxy, $R^2$ represents cyano, $R^3$ represents hydrogen, $R^4$ represents $C_1$-$C_6$-alkylcarbonyl, $C_1$-$C_6$-alkoxycarbonyl, hydroxycarbonyl, aminocarbonyl, mono- or di-$C_1$-$C_4$-alkylaminocarbonyl or cyano, wherein $C_1$-$C_6$-alkylcarbonyl, $C_1$-$C_6$-alkoxycarbonyl and mono-$C_1$-$C_4$-alkylaminocarbonyl can be substituted with one to three identical or different radicals selected from the group consisting of $C_3$-$C_6$-cycloalkyl, hydroxy, $C_1$-$C_4$-alkoxy, $C_1$-$C_4$-alkoxycarbonyl, amino, mono- or di-$C_1$-$C_4$-alkylamino, heteroaryl and heterocyclyl, $R^5$ represents methyl or ethyl, $R^{6a}$ represents hydrogen, $C_1$-$C_6$-alkylcarbonyl or $C_3$-$C_6$-cycloalkylcarbonyl, wherein $C_1$-$C_6$-alkylcarbonyl can be substituted with a radical selected from the group consisting of $C_3$-$C_6$-cycloalkyl, hydroxy, $C_1$-$C_4$-alkoxy, amino, mono- and di-$C_1$-$C_4$-alkylamino, $R^7$ represents halogen, nitro, cyano, trifluoromethyl, trifluoromethoxy, methyl or ethyl, and $Y^1$, $Y^2$, $Y^3$ and $Y^4$ each represent CH.

4. The compound of formula (I-A) according to claim 1, wherein

A represents a phenyl ring, $R^1$ and $R^3$ each represent hydrogen, $R^2$ represents cyano, $R^4$ represents $C_1$-$C_4$-alkylcarbonyl or $C_1$-$C_4$-alkoxycarbonyl, wherein $C_1$-$C_4$-alkoxycarbonyl can be substituted with a radical selected from the group consisting of hydroxy, $C_1$-$C_4$-alkoxy, $C_1$-$C_4$-alkoxycarbonyl, mono- and di-$C_1$-$C_4$-alkylamino, heteroaryl and heterocyclyl, $R^5$ represents methyl, $R^{6a}$ represents hydrogen, $C_1$-$C_6$-alkylcarbonyl or $C_3$-$C_6$-cycloalkylcarbonyl, $R^7$ represents trifluoromethyl or nitro, and $Y^1$, $Y^2$, $Y^3$ and $Y^4$ each represent CH.

5. The compound of general formula (I-A) according to claim 1, wherein $R^1$ is hydrogen.

6. The compound of formula (I-A) according to claim 1, wherein $R^4$ is $C_1$-$C_4$-alkoxycarbonyl, which can be substituted with dimethylamino, diethylamino, N -ethylmethylamino, pyrrolidino or piperidino, or wherein $R^4$ is $C_1$-$C_4$-alkylcarbonyl.

7. The compound of formula (I-A) according to claim 1, wherein $R^5$ is methyl.

8. The compound of formula (I-A) according to claim 1, wherein $R^7$ is trifluoromethyl or nitro.

9. The compound of formula (I-A) according to claim 1, wherein $R^{6a}$ is hydrogen.

10. A compound of formula (I-C)

(I-C)

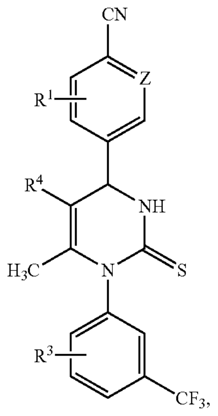

wherein

Z represents CH, and $R^1$, $R^3$ and $R^4$ have the meaning indicated in claim 1.

11. A composition containing at least one compound of formula (I-A) or (I-C), as defined in claims 1 or 10, and a pharmacologically acceptable diluent.

* * * * *